(12) United States Patent
Koleszar et al.

(10) Patent No.: US 6,643,634 B2
(45) Date of Patent: *Nov. 4, 2003

(54) GRAPHICAL VIEWER FOR BIOMOLECULAR SEQUENCE DATA

(75) Inventors: Alex George Koleszar, Newark, CA (US); Frank D. Russo, Sunnyvale, CA (US); Joe Don Heath, Sunnyvale, CA (US); Stephanie F. Berry, San Jose, CA (US); Rachel J. Wright, Mountain View, CA (US); Peter A Covitz, San Francisco, CA (US); Yvonne R. Boldt, Sunnyvale, CA (US); Lee Crawford, San Francisco, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/309,378

(22) Filed: Dec. 2, 2002

(65) Prior Publication Data

US 2003/0084023 A1 May 1, 2003

Related U.S. Application Data

(63) Continuation of application No. 09/362,649, filed on Jul. 27, 1999, now Pat. No. 6,519,583, which is a continuation-in-part of application No. 08/856,647, filed on May 15, 1997, now Pat. No. 5,970,500, and a continuation-in-part of application No. 08/857,382, filed on May 15, 1997, now Pat. No. 5,966,712.

(51) Int. Cl.[7] .............................................. G06F 17/30
(52) U.S. Cl. ................................ 707/1; 345/765; 435/6
(58) Field of Search ...................... 707/1, 6, 10, 104.1, 707/3; 435/6; 345/764, 765

(56) References Cited

U.S. PATENT DOCUMENTS

| | | | |
|---|---|---|---|
| 5,418,944 A | 5/1995 | DiPace et al. | 707/3 |
| 5,523,208 A | 6/1996 | Kohler et al. | 435/6 |
| 5,681,285 A | 10/1997 | Ford et al. | 604/151 |
| 5,701,256 A | 12/1997 | Marr et al. | 702/20 |
| 5,706,498 A | 1/1998 | Fujimiya et al. | 707/6 |
| 5,840,484 A | 11/1998 | Seilhamer et al. | 435/6 |
| 5,840,562 A | 11/1998 | Diep et al. | 435/212 |
| 5,953,727 A | 9/1999 | Maslyn et al. | 707/104.1 |
| 5,970,500 A | 10/1999 | Sabatini et al. | 707/104.1 |
| 6,023,659 A | 2/2000 | Seilhamer et al. | 702/19 |

FOREIGN PATENT DOCUMENTS

| | | |
|---|---|---|
| EP | 0 848 067 A2 | 6/1998 |
| WO | WO/96/23078 | 1/1996 |

OTHER PUBLICATIONS

Duret, et al., "HOVERGEN: a database of homologous vertebrate genes", Nucleic Acids Research, Revised and Accepted May 10, 1994, vol. 22, No. 12, pp. 2360–2365.

(List continued on next page.)

*Primary Examiner*—Jack M. Choules
(74) *Attorney, Agent, or Firm*—Beyer Weaver & Thomas, LLP

(57) ABSTRACT

Disclosed are methods, media and systems for graphically displaying computer-based biomolecular sequence information. Generally, biomolecular sequence information may be graphically depicted in a variety of different forms in accordance with the present invention. The sequence information may be composed of nucleotide or amino acid sequence information or both. The graphical depictions may be in several different formats providing different information relating to the sequences, and may be displayed in one or more screens of a computer user interface.

17 Claims, 22 Drawing Sheets

OTHER PUBLICATIONS

Larsen, et al., "The ribosomal database project", Nucleic Acids Research, 1993, vol. 21, No. 13, pp. 3021–3023.

D.W. Smith, et al., "Biocomputing: Informatics Genome Projects", Academic Press, Inc., Department of Biology and Center for Molecular Genetics, University of California, 1994, pp. 51–85.

Parsons, et al., "Clustering CDNA Sequences", CABIOS, 8(5) 461–466.

Henikoff, Steven, "Comparative Sequence Analysis: Finding Genes", Academic Press, Inc., 1994, pp. 867–111.

Schena, et al., "Parallel human genome analysis: Microarray–based expression monitoring of 1000 genes", Proc. Natl. Acad. Sci. USA, vol. 93, Oct. 1996, pp. 10614–10619.

Cuticchia, et al., "CMAP: contig mapping and analysis package, a relational database for chromosome reconstruction", Department of Genetics, The University of Georgia, vol. 8, No. 5, 1992, pp. 467–474.

Fickett, J.W. "Finding genes by computer: the state of the art" TIG vol. 12, No. 8, pp. 316–320. (Sep. 1996).

Honda, et al., "An Object Model for Genome Information at All Levels of Resolution", Jan. 1993, Proceedings of the Twenty–sixth Hawaii International Conference on System Sciences, vol. I, pp. 564–573.

Garner, "Engineering ins Genomiocs/ spl minus/ Automating the Gemone Center", May 1994, IEEE Engineering in Medicine and Biology Magazine, vol. 13, No. 2, pp. 281–283.

PathoSeq. 3.0 Dec. 97 Release Notes.

The Institute for Genomic Research, TIGR Database. Internet–http://www.tigr.org (Downloaded Dec. 23, 1997).

National Center for Biotechnology Information (Index). Internet–http://www3.ncbi.nlm.nih.gov/ (Downloaded Dec. 23, 1997).

National Center for Biotechnology Information; ENTREZ. Internet–http://www3.ncbi.nlm.nih.gov/entrez (Downloaded Dec. 23, 1997).

National Center for Biotechnology Information; UniGene. Internet–http://www3.ncbi.nlm.nih.gov/unigene (Downloaded Dec. 23, 1997).

National Center for Biotechnology Information; GenBank. Internet–http://www3.ncbi.nlm.nih.gov/web/genbank (Downloaded Dec. 23, 1997).

MAGPIE; Automated Genome Project Investigation Environment. Internet–http://www.mcs.anl.gov/home/gaasterl/magpie.html (Downloaded Dec. 23, 1997).

Stanford University, Stanford Genomic Resources. Internet–http://genome–www.stanford.edu, Sep. 1996 and Dec. 20, 1997.

Incyte Pharmaceuticals, LIFESEQ Version 4.2 Release Notes and Physical Data Model, Oct. 1996.

Incyte Pharmaceuticals, LIFESEQ Version 4.1 Release Notes and Physical Data Model, Jul. 1996.

Incyte Pharmaceuticals, LIFESEQ Version 3.4 Release Notes, Jan. 1996.

Incyte Pharmaceuticals, LIFESEQ Version 2.5 Release Notes, Jun. 1995.

Incyte Pharmaceuticals, LIFESEQ Version 3.0 Release Notes, Sep. 1995.

Incyte Pharmaceuticals, LIFESEQ Version 4.0 Release Notes, Apr. 1996.

Incyte Pharmaceuticals, *Introduction to the LIFESEQ Database*, Version 3.4, Jan. 1996.

Incyte Pharmaceuticals, *LIFESEQ Training Manual*, Version 4.1, Jul. 1996.

Green, et al., "Ancient Conserved Regions in New Gene Sequences and the Protein Databases", *Science*, v.259, n.5102, pp. 1711–1716 (1993).

Waldrop, et al., "Online Archives Lets Biologist Interrogate the Genome", *Science*, v. 269, n. 5229, pp. 1356–1358 (1995).

No Author, "Incyte Serves Up Information, part I", *In Vivo the Business & Medicine Report*, p.32, ISSN: 0258–851X (1996).

Martin, et al., "Accessing Genetics Databases", *Database*, v.17, n. 1, p. 51(8) (1994).

Matsubara, et al., "Identification of New Genes by Systematic Analysis of cDNAs and Database Construction", *Current Opinion in Biology*, vol. 4, pp. 672–677 (1993).

Lew, K., "GDB 6.0 Goals", *http://gbd.gbdnet.ad.jp/gdb/docs/gdb6–goals.html.*, pp. 1–5 (Mar. 3, 1996).

Kanehisa, M. "Toward Pathway Engineering: A New Database Old Genetic and Molecular Pathways." Science and Technology Japan, 1995, No. 59, pp. 34–38.

Gaasterland, T. and Sensen, C. "Using Multiple Tools for Automated Genome Interpretation in an Integrated Environment", Trends In Genetics, Jan. 1996.

*http://wehih.wehi.edu.au/* (1995).

Keele et al. "A Conceptual Database Model for Genomic Research", Journal of Computational Biology, vol. 1, No. 1 pp. 65–76 (1994).

Adams, M.D. et al. "Complementary DNA Sequencing: Expressed Sequence Tags and Human Genome Project", Science, Jun. 21, 1991, vol. 252, p. 1651–1656.

Keele et al., "A Conceptual Database Model for Genomic Research", 1994, Journal of Computational Biology, vol. 1, No. 1, pp. 65–76.

Mount, D.W. et al., "A Genomic Database for *Escherichia coli*: Total Information on a Given Organism" Academic Press BIOCOMPUTING 1994, pp. 249–266.

Yoshida, K. et al., "A Primer on Rapid Prototyping of Genomic Databases in Prolog." Academic Press BIOCOMPUTING, 1994, pp. 233–247.

Contig Results - Netscape

| Main Menu | Org Info | Genome | Contig Summary | Contig | Locus Info | Proteins | Comparisons | Southerns | Sequences | Help |

Contig Results

Library: SAUREU01  Staphylococcus aureus  Contigs: 48  Contigs ORFs: 134
Contig: SAU1c0039  Length: 138277 bp  Segs: 1846  Base Pairs Selected: 1 to 138277

| LocusID | Hit ID | Hit Description | Hit Organism | E-Value | Base Pairs | Libs (48) | Seqs |
|---|---|---|---|---|---|---|---|
| SAU102730 | g2633184 | yfth0 | Bacillus subtil | 3.4e-51 | 22-2169 (-) | 8 | 26 |
| SAU103442 | | LUR | | 1 | 2170-2722 () | 0 | 22 |
| SAU100689 | g2633977 | similar to hypothetical proteins | Bacillus subtil | 4.8e-62 | 2723-3559(+) | 24 | 30 |
| SAU102070 | g2633978 | ribonucleause H | Bacillus subtil | 3.2e-39 | 3594-4352(+) | 34 | 9 |
| SAU100241 | g2462967 | putative succinyl-coA synthetase beta ch | Bacillus subtil | 6.8e-123 | 4467-5621(+) | 35 | 13 |
| SAU100242 | g2633982 | succunyl-CoA synthetase (alpha subunit) | Bacillus subtil | 2.9e-97 | 5655-6542(+) | 35 | 10 |
| SAU102767 | g3767593 | LytN | Staphylococcus | 4.8e-23 | 6849-6998(+) | 3 | 7 |
| SAU101151 | g3767595 | Eprh | Staphylococcus | 0 | 7029-8270(+) | 13 | 18 |
| SAU101152 | g2633984 | ORF4 | Staphylococcus | 3.5e-109 | 8514-9314(+) | 36 | 13 |
| SAU101153 | g2462971 | DNA Topoisomerase I | Bacillus subtil | 0 | 9497-11563(+) | 48 | 32 |
| SAU101154 | g2633986 | Gid protein | Bacillus subtil | 0 | 11728-13026(+) | 43 | 36 |
| SAU101155 | g2633987 | integrase/recombinase | Bacillus subtil | 7.1e-51 | 13440-14333(+) | 38 | 27 |
| SAU101156 | g2633987 | beta-type subunit of the 20S proteasome | Bacillus subtil | 9.7e-52 | 14348-14881(+) | 21 | 17 |
| SAU101157 | g2633988 | ATP-dependent Clp protease-like | Bacillus subtil | 7.4e-95 | 14971-16350(+) | 40 | 16 |
| SAU101158 | g2633989 | transcriptional regulator | Bacillus subtil | 1.3e-62 | 16378-17139(+) | 9 | 8 |
| SAU100275 | g2634021 | ribosomal protein S2 | Bacillus subtil | 2.8e-73 | 17493-18200(+) | 47 | 12 |

GRAPHICAL VIEWER FOR BIOMOLECULAR SEQUENCE DATA

CROSS-REFERENCE TO RELATED APPLICATIONS

This is a Continuation application of prior application Ser. No. 09/362,649 now U.S. Pat. No. 6,519,583, filed on Jul. 27, 1999, designated the United States, the disclosure of which is incorporated herein by reference which is a continuation-in-part of application Ser. No. 08/856,647, filed May 15, 1997, entitled DATABASE AND SYSTEM FOR DETERMINING, STORING AND DISPLAYING GENE Locus INFORMATION, now U.S. Pat. No. 5,970,500, and application Ser. No. 08/857,382, filed May 15, 1997, entitled DATABASE AND SYSTEM FOR STORING, COMPARING AND DISPLAYING GENOMIC INFORMATION, now U.S. Pat. No. 5,966,712, the disclosures of which are incorporated by reference herein for all purposes.

BACKGROUND OF THE INVENTION

The present invention relates generally to the field of bioinformatics. In particular, the invention relates to methods, media and systems for graphically displaying computer-based biomolecular sequence information.

Informatics is the study and application of computer and statistical techniques to the management of information. Bioinformatics includes the development of methods to search computer databases of biomolecular sequence information (e.g., nucleic acid and protein) quickly, to analyze and display biomolecular sequence information, and to predict protein sequence, structure and function from DNA sequence data.

Increasingly, molecular biology is shifting from the laboratory bench to the computer desktop. Today's researchers require advanced quantitative analyses, database comparisons, and computational algorithms to explore the relationships between sequence and phenotype. Thus, by all accounts, researchers cannot and will not be able to avoid using computer resources to explore gene sequencing, gene expression, and molecular structure.

One use of bioinformatics involves studying an organism's genome to determine the sequence and placement of its genes and their relationship to other sequences and genes within the genome or to genes in other organisms. Such information is of significant interest in biomedical and pharmaceutical research, for instance to assist in the evaluation of drug efficacy and resistance. To make genomic information manipulation easy to perform and understand, sophisticated computer database systems have been developed. Incyte Pharmaceuticals, Inc. of Palo Alto, Calif., has developed several such databases, including some in which genomic sequence data is electronically recorded and annotated with information available from public sequence databases. Examples of such public sequence databases include GenBank (NCBI) and SWISSPROT. The resulting information is stored in a relational database that may be employed to determine relationships between sequences and genes within and among genomes.

While genetic data processing and relational database systems such as those developed by Incyte Pharmaceuticals, Inc. provide great power and flexibility in analyzing genetic information, further improvements in these systems will help accelerate biological research for numerous applications.

One area of interest in this regard is the display of biomolecular sequence information. As noted above, an important goal of genome research to determine the sequence and placement of a organism's genes and their relationship to other sequences and genes within the genome, to genes in other organisms, and to related protein sequences. The ability to clearly and effectively display gene loci information for a given organism or organisms would greatly assist this task.

Accordingly, the development of a display tool which allows a user to clearly and effectively display gene loci information for a given organism or organisms and/or other biomolecular sequence information is desirable.

SUMMARY OF THE INVENTION

The present invention meets this need by providing methods, media and systems for graphically displaying computer-based biomolecular sequence information. Generally, biomolecular sequence information may be graphically depicted in a variety of different forms in accordance with the present invention. The sequence information may be composed of nucleotide or amino acid sequence information or both. The graphical depictions may be in several different formats providing different information relating to the sequences, and may be displayed in one or more screens of a computer user interface.

A graphical viewer in accordance with the present invention preferably has a plurality of panels, each panel displaying information about the biomolecular sequence data of interest in a different way on a single screen or page. For example, a first panel could show a graphical representation of the entire biomolecular sequence, or the portion of the sequence of interest, with the locations of particular subsequences of interest indicated. A second panel could show a more detailed graphical representation of all or a selected portion of the sequence represented in the first window, allowing a user to focus on a particular subsequence of interest. This second panel view could depict additional information, such as annotations, relating to the particular subsequences of interest. A third panel could show information graphically representing the confidence level or origination, for example, of the biomolecular sequence data represented in one or more of the other panels. Additional panels on the same or additional screens could show, for example, the actual nucleotide or amino acid sequence of or relating to a selected subsequence of interest represented in one or more of the other panels, or other information relating to the biomolecular sequence data.

In one preferred embodiment, a graphical viewer in accordance with the present invention provides a graphical representation of all or a selected portion of an organism's genome with its individual loci indicated. The viewer allows the user to focus on a particular region or locus of interest and have it also be graphically represented with additional information, such as annotations. A graphical depiction of sequence coverage for the sequence regions represented in the viewer may also be provided.

The viewer may also provide for the display of related loci from other portions of the organism's genome (i.e., paralogs), and allows for the retrieval of information about the loci, such as actual nucleotide sequences or detailed annotations, from an associated relational database system. In addition, a graphical viewer in accordance with the present invention may provide for the graphical representation and comparison of multiple portions of the genome of one or more organisms based on a locus of interest and its corresponding paralogs and homologs (related loci from another organism's genome).

A graphical viewer in accordance with a preferred embodiment of the present invention preferably provides graphical representations of the genomic data in a plurality of panels, each panel displaying information about the genomic data of interest in a different way. In a particularly preferred embodiment of the invention, the graphical viewer has three main panels on a single screen: a legend viewer, which shows the entire portion of the genome under consideration; a target viewer, which allows a user to focus ("zoom in") on areas of the genome portion of particular interest; and a sequence depth viewer, which contains graphical information illustrating the depth of coverage over the length of the genome portion under consideration.

In one aspect, the present invention provides a method implemented in a computer system for presenting biomolecular sequence data. The method involves retrieving biomolecular sequence data from a database in response to a user query, and graphically depicting elements of the biomolecular sequence data in a user interface for the computer system. The graphical depiction may include a plurality of panels representing different aspects of the biomolecular sequence data in a single frame.

In a preferred embodiment, the biomolecular sequence data my include gene locus data and be graphically depicted in three panels, the first panel graphically depicting at least a portion of a contig and its associated loci, the second panel graphically depicting at least a portion of the contig depicted in the first panel and annotated loci associated with the portion, and the third panel graphically depicting information indicating the number of sequencing operations conducted to determine the sequence data depicted in the second panel. The third panel may graphically depicts sequences used to assemble the portion of the contig depicted in the second panel, or depth of coverage information for the portion of the contig depicted in the second panel.

In another aspect, the invention provides another method implemented in a computer system for presenting biomolecular sequence data. The method involves retrieving biomolecular sequence data for a plurality of homologous loci from a database in response to a user query, and graphically depicting at least some of the homologous loci in a user interface for the computer system.

In yet another aspect, the invention provides a computer system. The computer system includes a database including biomolecular sequence data, and a user interface. The user interface is capable of receiving a query relating to the biomolecular sequence data, and graphically displaying the results of the query.

In still another aspect, the invention provides a computer-readable medium containing programmed instructions arranged to graphically display biomolecular sequence data. The computer-readable medium includes programmed instructions for retrieving biomolecular sequence data from a computer system database in response to a user query, and graphically depicting elements of the biomolecular sequence data in a user interface for the computer system.

These and other features and advantages of the present invention will be presented in more detail in the following specification of the invention and the accompanying figures which illustrate by way of example the principles of the invention.

BRIEF DESCRIPTION OF THE DRAWINGS

FIG. 2 is a screen shot (HTML page) depicting a Contig Results page for a graphical user interface of a genomic sequences database suitable for selecting a locus to be viewed with a biomolecular sequence graphical viewer in accordance with one embodiment of the present invention.

DETAILED DESCRIPTION OF PREFERRED EMBODIMENTS

Figure 1A:
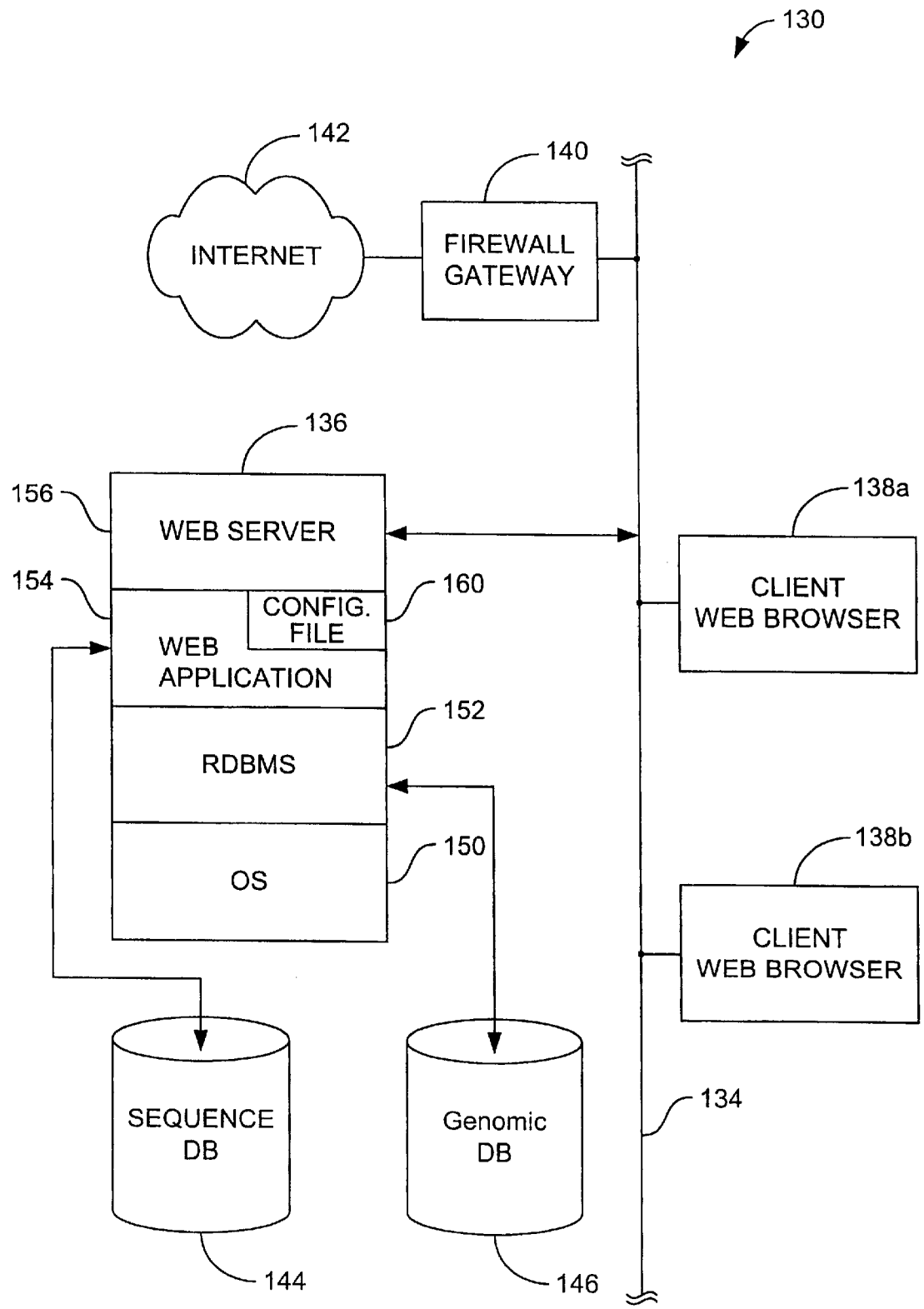
FIG. 1A is a block diagram of a client-server Intranet for providing database services in accordance with one embodiment of the present invention.

Reference will now be made in detail to preferred embodiments of the invention. Examples of the preferred embodiments are illustrated in the accompanying drawings. While the invention will be described in conjunction with these preferred embodiments, it will be understood that it is not intended to limit the invention to one or more preferred embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Introduction

The present invention provides methods, media and systems for graphically displaying computer-based biomolecular sequence information. Generally, biomolecular sequence information may be graphically depicted in a variety of different forms in accordance with the present invention. The sequence information may be composed of nucleotide or amino acid sequence information or both. The graphical depictions may be in several different formats providing different information relating to the sequences, and may be displayed in one or more screens of a computer user interface.

A graphical viewer in accordance with the present invention preferably has a plurality of panels, each panel displaying information about the biomolecular sequence data of interest in a different way on a single screen or page. For example, a first panel could show a graphical representation of the entire biomolecular sequence, or the portion of the sequence of interest, with the locations of particular subsequences of interest indicated. A second panel could show a more detailed graphical representation of all or a selected portion of the sequence represented in the first window, allowing a user to focus on a particular subsequence of interest. This second panel view could depict additional information, such as annotations, relating to the particular subsequences of interest. A third panel could show information graphically representing the confidence level or origination, for example, of the biomolecular sequence data represented in one or more of the other panels. Additional panels on the same or additional screens could show, for example, the actual nucleotide or amino acid sequence of or relating to a selected subsequence of interest represented in one or more of the other panels, or other information relating to the biomolecular sequence data.

In one preferred embodiment, a graphical viewer in accordance with the present invention provides a graphical representation of all or a selected portion of an organism's genome with its individual loci indicated. The viewer allows the user to focus on a particular region or locus of interest and have it also be graphically represented with additional information, such as annotations. A graphical depiction of sequence coverage for the sequence regions represented in the viewer may also be provided.

The viewer also may also provide for the display of related loci from other portions of the organism's genome (i.e., paralogs), and allows for the retrieval of information about the loci, such as actual nucleotide sequences or detailed annotations, from an associated relational database system. In addition, a graphical viewer in accordance with the present invention may provide for the graphical representation and comparison of multiple portions of the genome of one or more organisms based on a locus of interest and its corresponding paralogs and homologs (related loci from another organism's genome).

A graphical viewer in accordance with a preferred embodiment of the present invention preferably provides graphical representations of the genomic data in a plurality of panels, each panel displaying information about the genomic data of interest in a different way. In a particularly preferred embodiment of the invention, the graphical viewer has three main panels on a single screen: a legend viewer, which always shows the entire portion of the genome under consideration; a target viewer, which allows a user to focus ("zoom in") on areas of the genome portion of particular interest; and a sequence depth viewer, which contains graphical information illustrating the depth of coverage over the length of the genome portion under consideration.

Of course, as noted above, a graphical viewer in accordance with the present invention may be used to display biomolecular sequence information other than the gene locus information described with reference to the preferred embodiments of the invention described herein. For example, a graphical viewer in accordance with the present invention may be used to display peptide or nucleotide sequence information, and can be used to display actual sequences resulting from comparisons of sequences from, for example, a BLAST or FASTA search.

The Graphical Viewer Environment

Figure 1B:
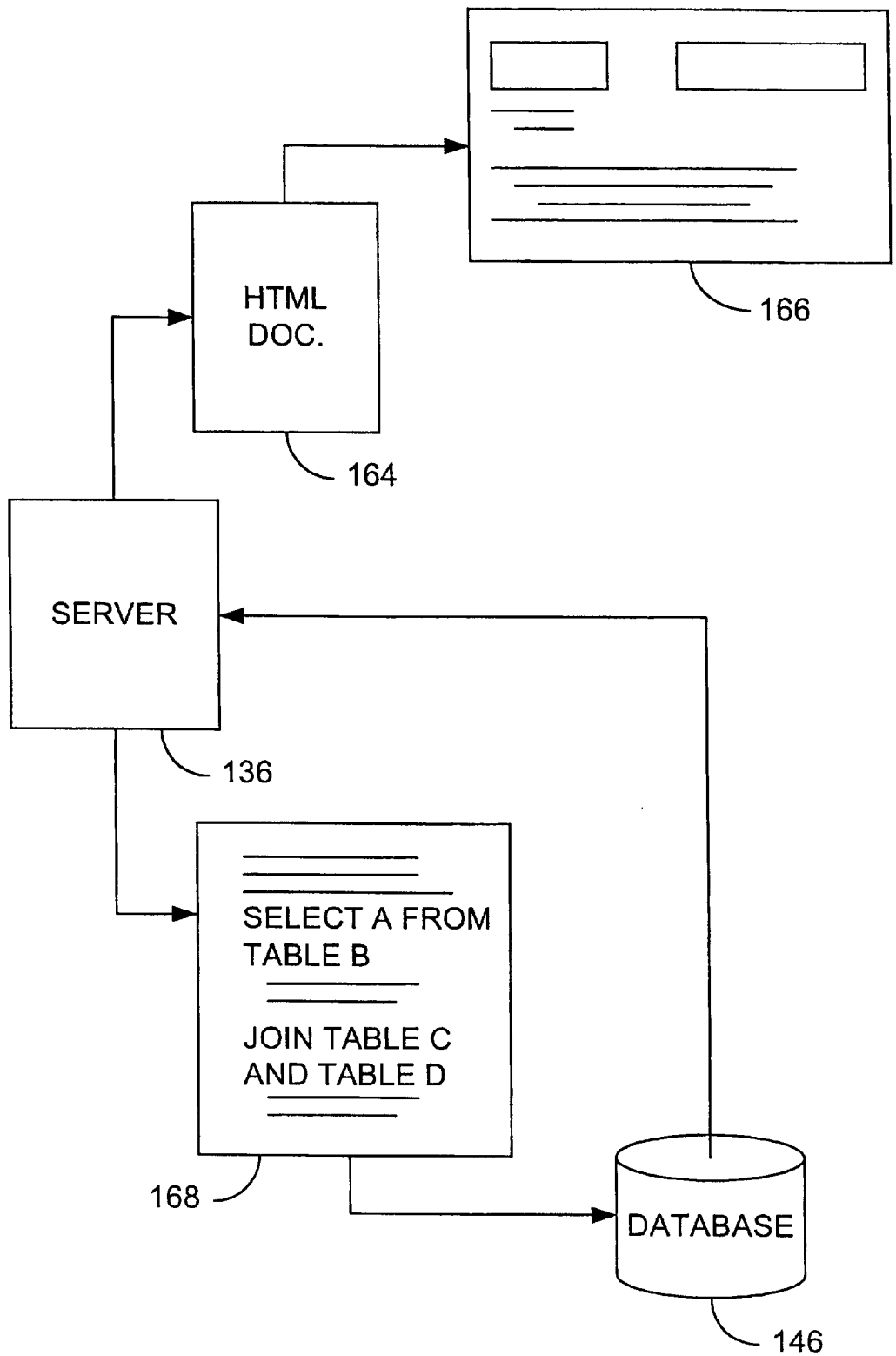
FIG. 1B is a schematic representation of the various software documents and entities employed by the FIG. 1A client-server Intranet to provide biological information in response to user queries.

As noted above, a graphical viewer in accordance with the present invention is preferably used in connection with a biomolecular sequence relational database system, such as those developed by Incyte Pharmaceuticals, Inc. of Palo Alto, Calif., and described, for example, in patent application Ser. Nos. 08/947,845, 08/856,647, 08/811,758, 08/812,290 and 08/857,382, the disclosures of which are incorporated by reference herein for all purposes. Data to be displayed by a graphical viewer in accordance with the present invention is accessed from such a database system using techniques and commands well known to those of skill in the art. FIGS. 1A and 1B and the associated description provided below provide a context in which a graphical viewer in accordance with the present invention may operate.

FIG. 1A depicts a network system 130 suitable for storing and retrieving information in relational databases, such as those suitable for supporting a graphical viewer in accordance with the present invention. Network 130 includes a network cable 134 to which a network server 136 and clients 138a and 138b (representative of possibly many more clients) are connected. Cable 134 is also connected to a firewall/gateway 140 which is in turn connected to the Internet 142.

Network 130 may be any one of a number of conventional network systems, including a local area network (LAN) or a wide area network (WAN), as is known in the art (e.g., using Ethernet, IBM Token Ring, or the like). The network includes functionality for packaging client calls in a well-known format (e.g., URL) together with any parameter information into a format (of one or more packets) suitable for transmission across a cable or wire 134, for delivery to database server 136.

Server 136 includes the hardware necessary for running software to (1) access database data for processing user requests, and (2) provide an interface for serving information to client machines 138a and 138b. In a preferred embodiment, depicted in FIG. 1A, the software running on the server machine supports the World Wide Web protocol for providing page data between a server and client. In this embodiment, a web server 156 having URL and HTTP functionality communicates with a client via the HTTP protocol.

Client/server environments, database servers, relational databases and networks are well documented in the technical, trade, and patent literature. For a discussion of database servers, relational databases and client/server environments generally, and SQL servers particularly, see, e.g., Nath, A., *The Guide To SQL Server*, 2nd ed., Addison-Wesley Publishing Co., 1995 (which is incorporated herein by reference for all purposes).

As shown, server 136 includes an operating system 150 (e.g., UNIX) on which runs a relational database management system 152, a World Wide Web application 154, and a World Wide Web server 156. The software on server 136 may assume numerous configurations. For example, it may be provided on a single machine or distributed over multiple machines.

World Wide Web application 154 includes the executable code necessary for generation of database language statements (e.g., Standard Query Language (SQL) statements). Generally, the executables will include embedded SQL statements. In addition, application 154 includes a configuration file 160 which contains pointers and addresses to the various software entities that comprise the server as well as the various external and internal databases which must be accessed to service user requests. Configuration file 160 also directs requests for server resources to the appropriate hardware—as may be necessary should the server be distributed over two or more separate computers.

Each of clients 138a and 138b includes a World Wide Web browser for providing a user interface to server 136, and including code necessary to generate HTML pages. Through the Web browser, clients 138a and 138b construct search requests for retrieving data from a sequence database 144 and/or a genomic database 146, for example. Thus, the user will typically point and click to user interface elements such as buttons, pull down menus, scroll bars, etc. conventionally employed in graphical user interfaces. The requests so formulated with the client's Web browser are transmitted to Web application 154 which formats them to produce a query that can be employed to extract the pertinent information from sequence database 144 or genomic database 146.

In the embodiment shown, the Web application accesses data in genomic database 146 by first constructing a query in a database language (e.g., Sybase or Oracle SQL). The database language query is then handed to relational database management system 152 which processes the query to extract the relevant information from database 146. In the case of a request to access sequence database 144, Web application 154 directly communicates the request to that database without employing the services of database management system 152.

The procedure by which user requests are serviced is further illustrated with reference to FIG. 1B. In this embodiment, the World Wide Web server and/or executable Web application components of server 136 provide Hypertext Mark-up Language documents ("HTML pages") 164 to a client machine. At the client machine, the HTML document provides a user interface 166 which is employed by a user to formulate his or her requests for access to database 146. That request is converted by the Web application component of server 136 to a SQL query 168. That query is used by the database management system component of server 136 to access the relevant data in database 146 and provide that data to server 136 in an appropriate format. Server 136 then generates a new HTML document, possibly through the Web application 154, relaying the database information to the client as a view in user interface 166.

While the embodiment shown in FIG. 1A employs a World Wide Web server and World Wide Web browser for a communication between server 136 and clients 138a and 138b, other communications protocols will also be suitable. For example, client calls may be packaged directly as SQL statements, without reliance on Web application 154 for a conversion to SQL. Clients may also query the database directly without using a client browser.

When network 130 employs a World Wide Web server and clients, it must support a TCP/IP protocol. Local networks such as this are sometimes referred to as "Intranets." An advantage of such Intranets is that they allows easy communication with public domain databases residing on the World Wide Web (e.g., the GenBank World Wide Web site). Thus, in a particular preferred embodiment of the present invention, clients 138a and 138b can directly access data (via Hypertext links for example) residing on Internet databases using a HTML interface provided by Web browsers and Web server 156.

Bear in mind that if the contents of the local databases are to remain private, a firewall 140 must preserve in confidence the contents of a sequence database 144 and a genomic database 146.

In a preferred embodiment, sequence database 144 is a flat file database with a single file for genomic sequences from different species. Other possible approaches may include partitioning the sequence data according to different species or whether or not sequences have been found to be unique to the local database (i.e., sequences that did not have any hits in an external database such as GenBank).

Preferably, the information in genomic database 146 is stored in a relational format. Such a relational database supports a set of operations defined by relational algebra. It generally includes tables composed of columns and rows for the data contained in the database. Each table has a primary key, being any column or set of columns the values of which uniquely identify the rows in the table. The tables of a relational database may also include a foreign key, which is a column or set of columns the values of which match the primary key values of another table. A relational database is also generally subject to a set of operations (select, project, product, join and divide) which form the basis of the relational algebra governing relations within the database. As noted above, relational databases are well known and documented (see, e.g., Nath, A., *The Guide To SQL Serve*, referenced above).

A relational database may be implemented in different ways. In Oracle™ databases, for example, the various tables are not physically separated, as there is one instance of work space with different ownership specified for different tables. In Sybase™ databases, in contrast, the tables may be physically segregated into different "databases."

One specific configuration for network 130 for multiple users provides both the genomic and sequence databases on the same machine. If there is a high volume of sequence searching, it may be desirable to have a second processor of similar size and split the application across the two machines to improve response time.

A suitable dual processor server machine may be any of the following workstations: Sun—Ultra-Sparc 2™ (Sun Microsystems, Inc. of Mountain View, Calif.), SGI—Challenge L™ (Silicon Graphics, Inc. of Mountain View, Calif.), and DEC—2100A™ (Digitial Electronics Corporation of Maynard, Mass.). Multiprocessor systems (minimum of 4 processors to start) may include the following: Sun—Ultra Sparc Enterprise 4000™, SGI-Challenge XL™, and DEC—8400™. Preferably, the server machine is configured for network 130 and supports TCP/IP protocol.

Depending upon the workstation employed, the operating system may be, for example, one of the following: Sun—Sun OS 5.5 (Solaris 2 5), SGI—IRIX 5 3 (or later), or DEC—Digital UNIX 3 2D (or later).

Databases used in conjunction with this invention may be downloaded via a 4×4 Gb+ FWSCSI-2, Fiber Link Raid Units 20Gb+, or 4 DAT Tape Drive. A CD ROM drive may also be acceptable.

The client machine may be, for example, a Macintosh™ (Apple Computer Inc. of Cupertino, Calif.), a PC, or a Unix workstation. It should also be TCP/IP capable with a Netscape or Internet Explorer Web Browser.

The network may include a 10Base-T, 100Base-T or higher connection, be TCP/IP capable, and provide access to Internet for HTML hyperlinks to external databases.

Figure 1C:
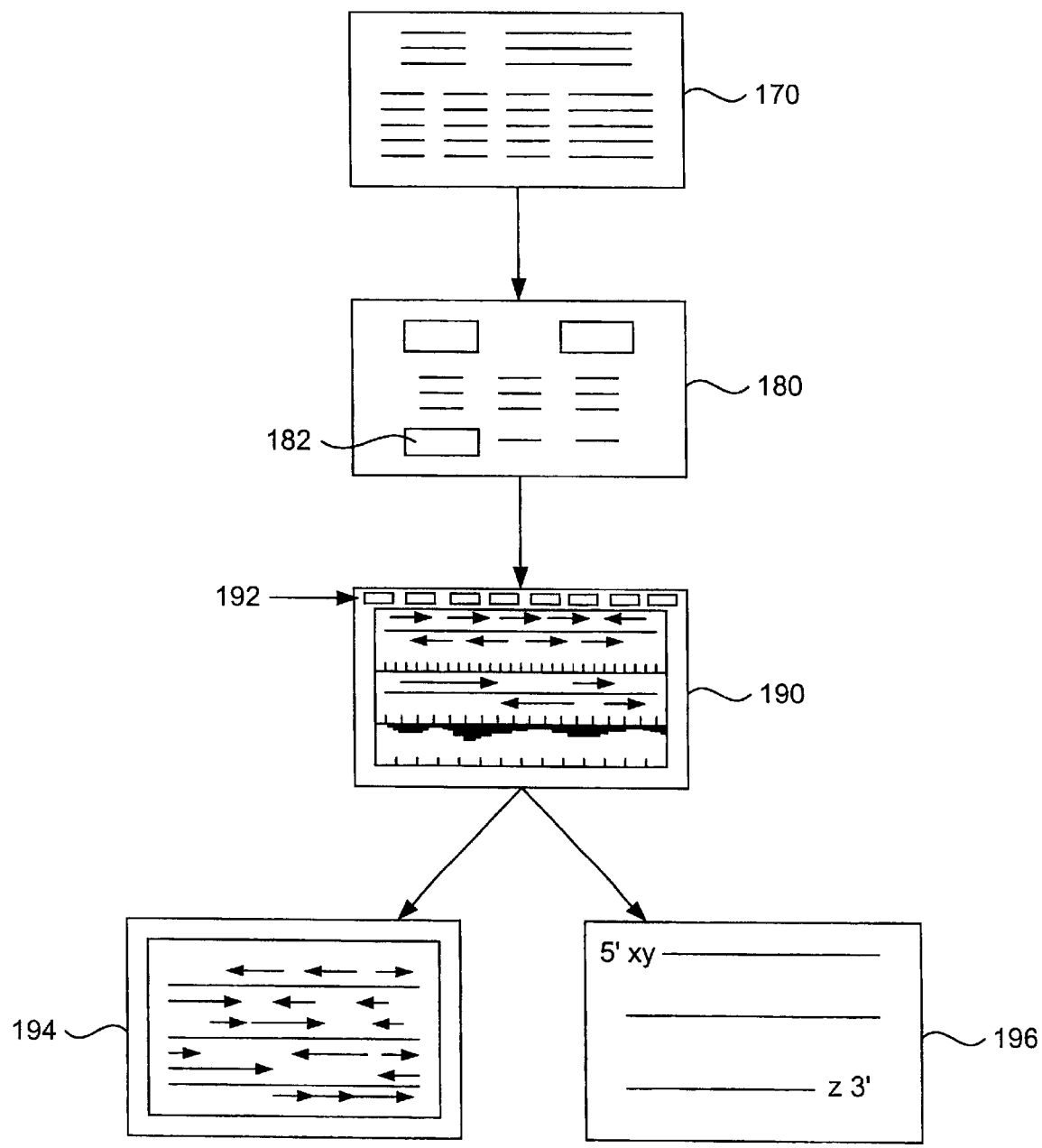
FIG. 1C is a block diagram illustrating the accessibility of graphical viewer features in accordance with a preferred embodiment of the present invention in connection with a biomolecular sequence database.

FIG. 1C illustrates the accessibility of graphical viewer features in accordance with a preferred embodiment of the present invention. A graphical viewer in accordance with the present invention is preferably provided together with a suite of functions made available to users through a collection of user interface screens (e.g., HTML or Java® pages) viewed in the user interface of a biomolecular relational database. Typically, the interface will have a main viewer page from which various lines of query can be followed. In a preferred embodiment, the main viewer page (and other graphical viewers) are Java®-based applets running on the network system. Given the functionalities described herein, one of ordinary skill in the art would be able to implement the graphical viewers of the present invention in Java® or other programming environments. The viewer page is typically accessed from another page provided as part of the user interface of a biomolecular sequence relational database in connection with which the graphical viewer is used.

For example, a user interface screen (e.g., HTML page) 170 displays textual information relating to a plurality biomolecular sequences. One or more sequences displayed in the page 170 may be selected, for example, using the pointer provided in the GUI, to access another page 180 which displays additional information about the selected sequences. This page 180 may include a button which when selected accesses a main graphical viewer page 190. The graphical viewer page (e.g., Java® page) 190 graphically depicts information about the selected sequences. The page also preferably includes buttons 192 which allow a user to modify the graphical display. The buttons 192 may also include buttons which a user may select to access additional graphical viewer pages 194, 196, which graphically or otherwise display additional information relating to the graphically displayed sequence information in page 190.

Gene Locus Implementation

The invention will now be described with reference to a particular preferred implementation of the invention to graphically depict gene locus information. The invention will be described with reference to a database optimized for microbial data, such as that described with reference to parent application Ser. No. 08/856,647, previously incorporated by reference. However, application of the present invention is by no means so limited. For example, the invention covers graphical viewers used in connection with databases optimized for other sources of biomolecular sequence data, such as animal sequences (e.g., human, primate, rodent, amphibian, insect, etc.) and plant sequences.

As noted above, a graphical viewer in accordance with the present invention is preferably provided together with a suite of functions made available to users through a collection of user interface screens viewed in the user interface of a biomolecular relational database. A main viewer page is typically accessed from another page provided as part of the user interface of a biomolecular sequence relational database in connection with which the graphical viewer is used, in this case a microbial genomic database. FIG. 2 depicts one such other page from the microbial genomic database. The Contig Results page 200 displays a list of loci (identified by their LocusIDs) for genes localized to a particular "contig" (a group of assembled overlapping sequences), contig SAU1c0039, of the genomic sequence of a microbial organism, in this case *Staphylococcus aureus*.

Figure 3:
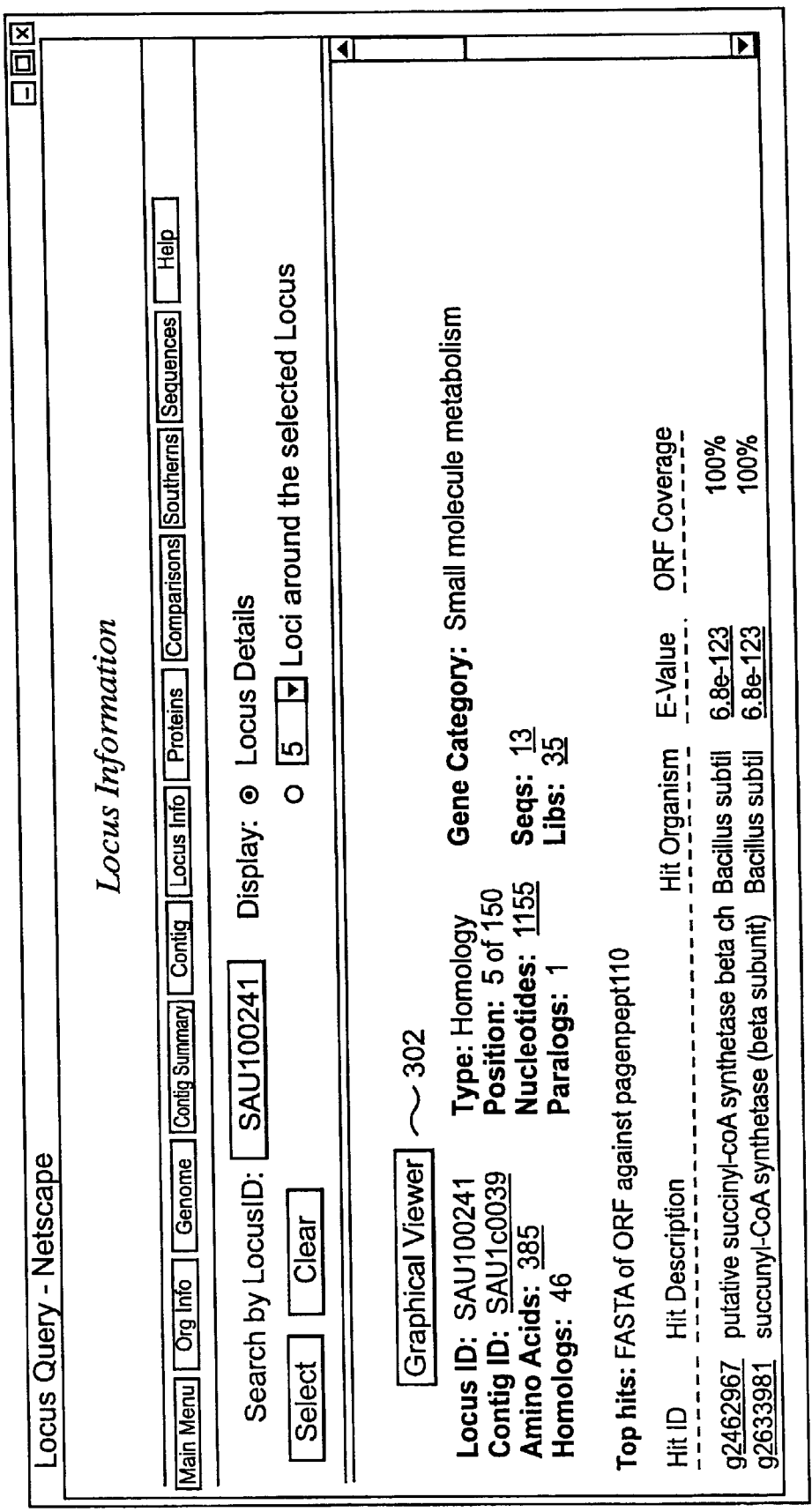
FIG. 3 is a screen shot depicting a Locus Information page for a graphical user interface of a genomic sequences database suitable for accessing a biomolecular sequence graphical viewer in accordance with one embodiment of the present invention.

By clicking on a particular LocusID in Contig Results page 200, a user accesses a Locus Information page, such as depicted in FIG. 3. Clicking on the LocusID SAU100241 in page 200, returns the Locus Information page 300 which displays details about the locus SAU100241. The page also displays a Graphical Viewer button 302 which when selected launches a graphical viewer in accordance with the present invention.

Figure 4A:
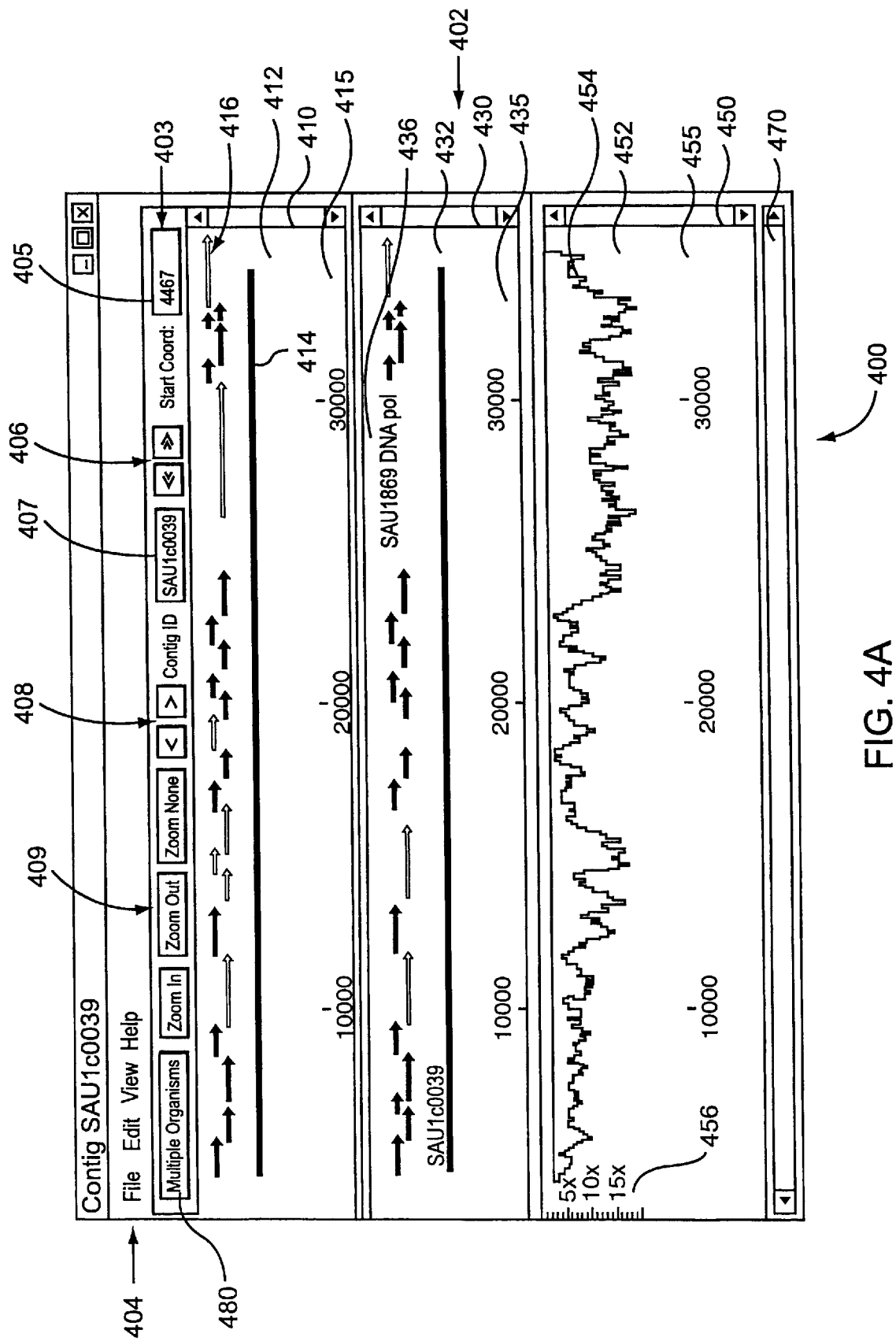
FIG. 4A is a screen shot depicting a main page of a biomolecular sequence graphical viewer in accordance with one embodiment of the present invention.

FIG. 4A depicts a main graphical viewer page 400 accessed by selecting the Graphical Viewer button 302 in Locus Information page 300. In this preferred embodiment, the graphical viewers are Java®-based applets that provide a graphical representation of a portion of a contig and its related loci. A graphical viewer in accordance with the present invention preferably includes a plurality of separate component viewers. Where more than one component viewer is featured it is preferably displayed in a single frame in order to enhance the effectiveness with which the graphically displayed data is conveyed to the user. A preferred embodiment includes three component viewers displayed in a single frame.

Thus, the graphical viewer 402 of page 400 has three viewer component panels on a single screen. The top panel 410 features a "legend viewer" 412, which shows the entire portion of the genome under consideration. The middle panel 430 features a "target viewer" 432, which allows a user to focus ("zoom in") on areas of the genome portion of particular interest. The bottom panel 450 features a "sequence depth viewer" 452, which contains graphical information illustrating the depth of coverage over the length of the genome portion represented in the target viewer 422.

The graphical viewer page 400 also includes several buttons and windows along the top 403 of the page 400 for accessing and displaying additional information. A menu bar 404 is also provided for accessing pull-down menus listing various command and control functions. A scale 415, 435, 455 depicted at the bottom of each viewer panel 410. The use of these features will be described in further detail below.

The legend viewer 412 always shows the entire portion of the contig which was loaded by the viewer when the user selected a contig in the previous screens. In a preferred embodiment, the viewer will load a predetermined default number of base pairs of the contig sequence. If the contig is shorter than the default, the entire contig will be depicted and the default will be adjusted. For example, in this embodiment, the viewer loads 30,000 base pairs starting at the first locus in the list on the Contig Results screen 200 (identified by its Hit ID), g2462967. The number of base pairs shown and the position on the contig may be determined with reference to the scale 415 depicted at the bottom of the legend viewer panel 410. The default value may, of course, be changed to any desired number.

The legend viewer 412 graphically represents contig SAU1c0039 as a line 414 which starts at coordinate (base pair number) 4467 and extends up to coordinate 34,467, as may be seen with reference to the scale 415. The contig depicted in the viewer is identified in a ContigID window 407. In addition, the starting coordinate for the portion of the contig depicted by the legend viewer 412 (namely, the starting coordinate of the selected locus g2462967: 4467) is noted in the Start Coord window 405. These windows 405, 407 may also be used to enter information in order to control the information depicted by the viewer, as described further below. A user may bring upstream or downstream portions of the contig into view in the legend viewer 412, and the other component viewers, by clicking on the directional buttons 406.

In addition to the contig, the legend viewer 412 shows the various loci residing on the portion of the contig. The manner in which these loci are depicted illustrates the power of a graphical viewer in accordance with the present invention in presenting information in a highly effective manner.

The loci are represented by arrows 416. Each loci is located beside the contig line 414 according to its position on the contig and the direction in which it is read. The arrowhead represents the direction in which a locus is read. Loci which are read in the forward (+) direction are depicted above the contig line 414. Loci which are read in the reverse (−) direction are depicted below the contig line 414. In addition, other graphical features may be used to convey information about the graphically depicted loci. For example, loci for which the sequences obtained are above an established confidence threshold may be depicted as broken arrows.

In this preferred embodiment, the loci are also represented in different colors based on their protein's function. Proteins are grouped into various functional categories, with each category being assigned a color. For example, in this preferred embodiment, the proteins corresponding to loci are grouped according to the following categories/colors: Motility/Light blue; Virulence/Red; Transport/Light Green; Regulation/Magenta; Macromolecule metabolism/Yellow; Small molecule metabolism/Dark blue; Structure/Dark Green; and Unclassified/Black. Of course other categories and colors may also be used. These arrow and color representation features for loci are used in both the legend viewer and the target viewer, discussed below.

The target viewer 432 initially displays the same scope as the legend viewer 412. The scope of the target viewer may be modified, however, by clicking on the Zoom buttons 409. The Zoom In button provides a closer view of a portion of the contig shown in the legend viewer 412. The closer view is depicted in the target viewer 432, with the scale 435 adjusting to reflect the amount of the zoom. The Zoom Out button provides a broader view of the contig, up to the maximum of the default base pair number selected for the legend viewer (minimum magnification). The Zoom None button automatically returns to the minimum magnification.

Another way provided by a graphical viewer in accordance with the present invention to focus on a portion of interest of a contig 414 depicted in the legend viewer 412 is to provide an outline, such as a colored (e.g., red) box, around the portion of the contig 414 which is shown in the target viewer 432. In this preferred embodiment, when a red box surrounds the entire legend viewer panel, the target viewer also display the entire 30,000 base pairs. This is the situation illustrated in FIG. 4A. When the Zoom buttons 409 are used, as described above, the red box is adjusted accordingly.

Figure 4B:
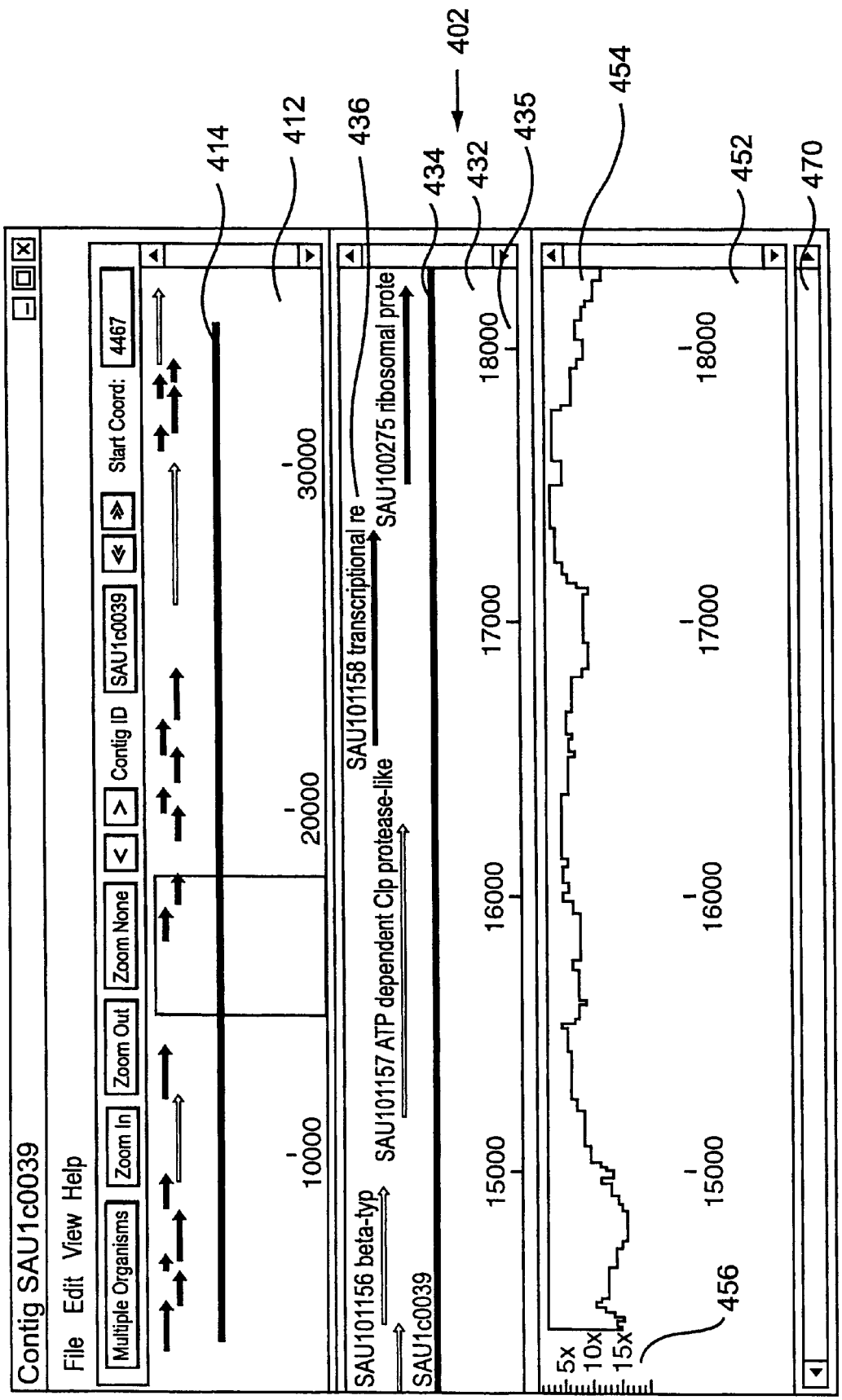
FIG. 4B is a screen shot depicting a main page of a biomolecular sequence graphical viewer modified to illustrate the zoom feature in accordance with one embodiment of the present invention.

An area on the contig may also be zoomed into by direct user adjustment of the red box (known as "rubber banding"). The scope of the red box may be changed by clicking at a location in any of the viewer panels and dragging the cursor with a mouse to another location. The red box will then encompass the region between those two points, and only this region will be visible in the target and sequence depth viewers. FIG. 4B depicts an updated page showing the viewer 402 after a user has zoomed in on the portion 434 of the contig 414 depicted in the legend viewer 412 between about the coordinates 14,200 and 18,200. The scale 435 at the bottom of the target viewer 432 has been adjusted to reflect the new scope of the zoomed target view.

Another feature of the target viewer is the loci are annotated. As may be seen in FIGS. 4A and 4B, annotations 436 are provided for loci arrows which are long enough to accommodate the annotation information. If a loci of interest is too short to be display its annotation, a user may zoom in further on the locus until it is long enough to allow the annotation to be displayed in the graphical representation.

Figure 5A:
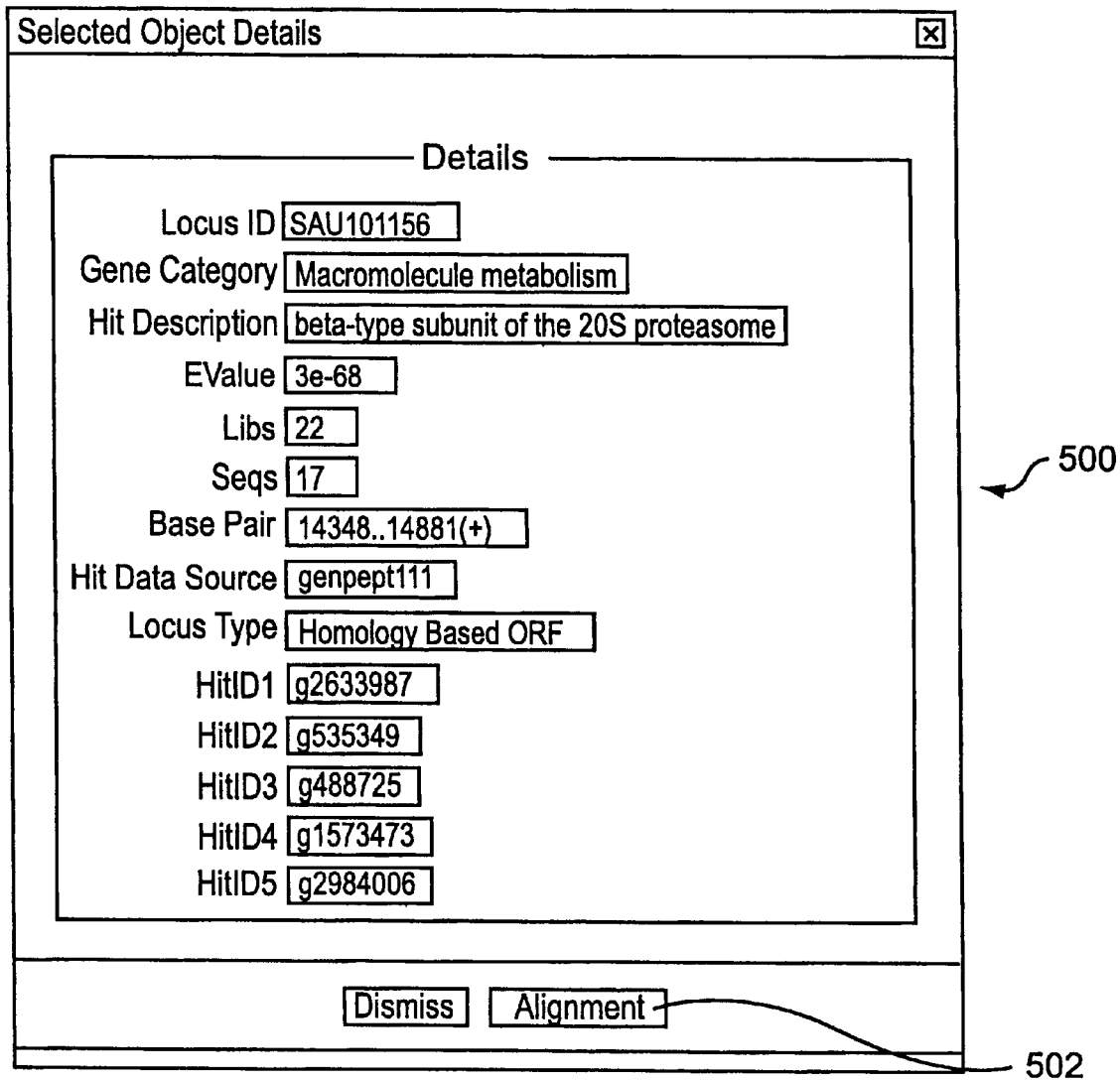
FIG. 5A is a Selected Object Details window in accordance with one embodiment of the present invention.

Individual loci in the target viewer 432 may be selected for further analysis by clicking on the graphically depicted locus. A selected locus is highlighted in some manner, for example, by displaying a colored (e.g., red) box around its representation. Details about this locus my be viewed by double-clicking on the locus representation. Double-clicking opens a Selected Object Details window, such as depicted in FIG. 5A. The Selected Object Details window 500 includes information about the locus, including its LocusID, gene (functional) category, base pair range, the sequence's homologous matches (preferably the number of homologous matches returned is limited to a preset number; for example, the top five matches are returned here) against other sequence databases, for example, the genpept database, and other information useful to researchers and relating to other features of the database system with which the graphical viewer is used. Many of the fields of information provided in the window 500 may be hyperlinks to other HTML pages or other screens.

Figure 5B:
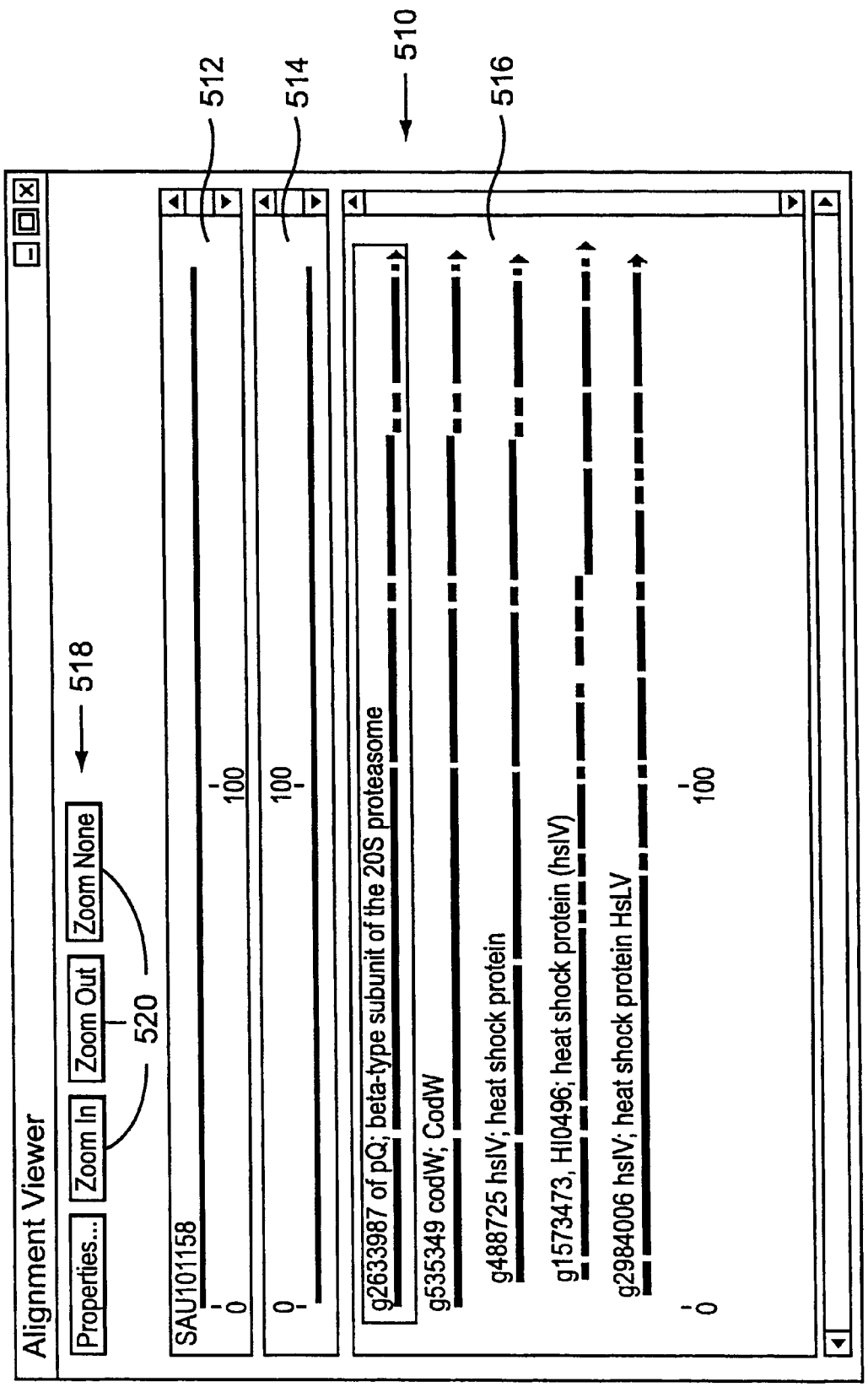
FIGS. 5B and 5C are screen shots depicting an alignment viewer in accordance with one embodiment of the present invention.
Figure 5C:
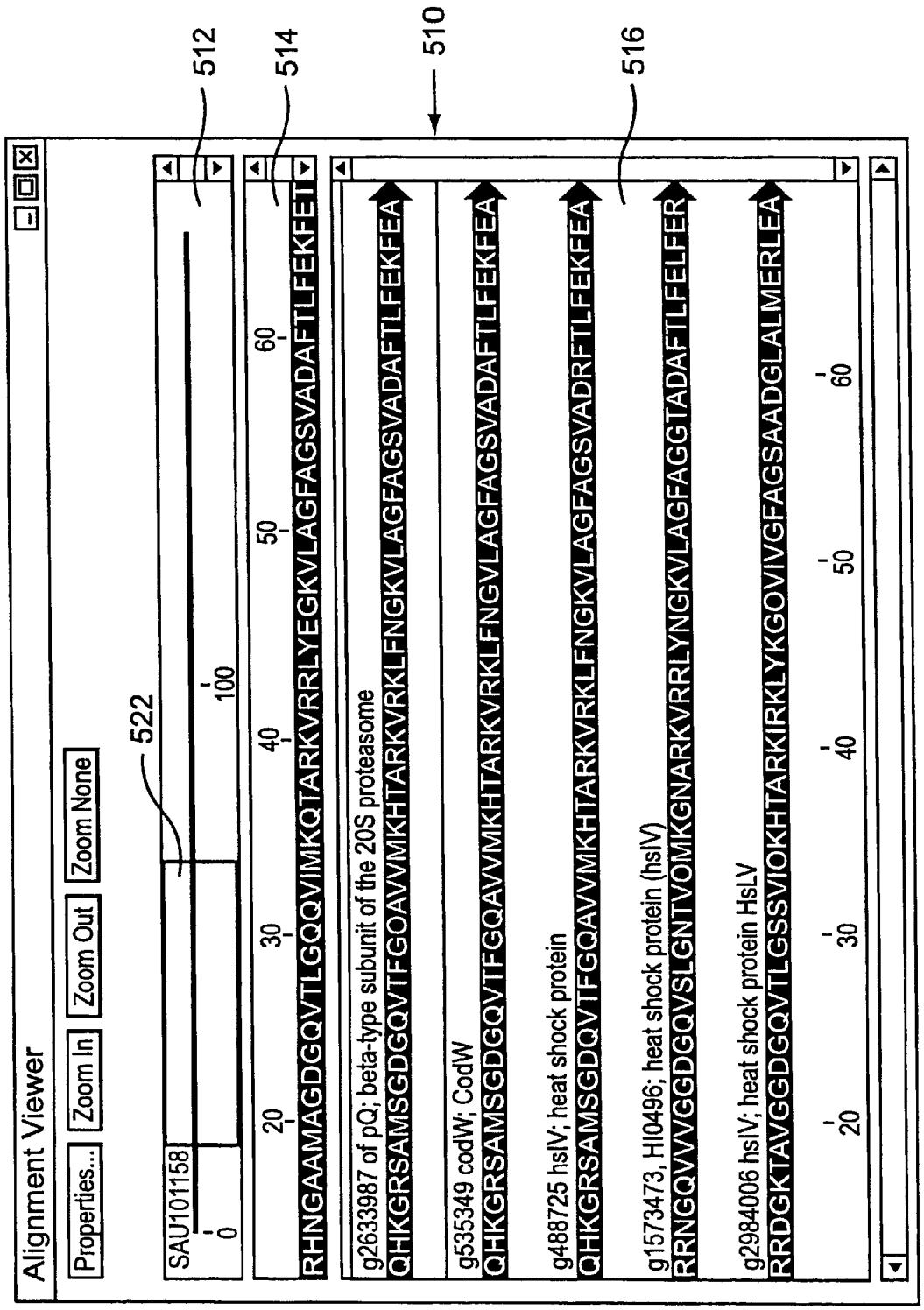

The Selected Object Details window 500 includes an Alignment button 502. Clicking on this button accesses an alignment viewer which provides a graphical representation of the locus sequence and its homologous matches. An example of an alignment viewer 510 in accordance with a preferred embodiment of the present invention is shown in FIG. 5B. The alignment viewer 510 has three panels. The top two panels 512 and 514 provide a graphical representation of the locus identified in FIG. 5A (SAU101156). The third panel 516 provides graphical representations of the five homologs noted in FIG. 5A. The alignment viewer page also includes a number of buttons 518 which may be used to control the graphical representations. In particular, the page has Zoom buttons 520 which may be used to zoom into the sequence level of loci depicted in the lower two panels 514 and 516 (while the upper panel 512 maintains the depiction of the entire locus). FIG. 5C illustrates this Zoom feature where the upper panel 512 has a colored box 522 around the portion of the locus depicted with its homologs at the sequence level in the two lower panels 514 and 516. In this embodiment, the amino acid sequences are shown. In other embodiments, the corresponding nucleotide sequences may also be shown.

An additional feature of the graphical viewer page 400 that becomes useful when the scope of the view in the target viewer 432 is focused in on a portion of the contig sequence shown in the legend viewer 412 is a scroll bar 470 at the bottom of the page. The scroll bar 470 allows a user to move along the portion 434 of the contig 414 to bring upstream or downstream portions of the contig 414 into view in the target viewer 432.

The third panel 450 of the graphical viewer 402 in this embodiment of the present invention is the sequence depth viewer 452. The sequence depth viewer 452 provides a graph illustrating the depth of coverage, that is, the number of times that a given portion of the contig has been sequenced, over the length of the contig. The sequence depth viewer 452 displays its graph for the contig or portion of the contig displayed in the target viewer 432. Thus, in FIG. 4A, were the target viewer 432 and legend viewer 412 have the same scope, the sequence depth viewer 452 displays a graph showing the depth of coverage over the 30,000 base pairs of the contig 414 from coordinates 4467 to 34,467, as indicated by the scale 455 at the bottom of the sequence depth viewer panel 450. In FIG. 4B, however, the sequence depth viewer 452 displays a graph showing the depth of coverage over the approximately 4000 base pairs of the portion 434 of the contig zoomed in on in the target viewer from about coordinates 14,200 to 18,200, as indicated by the adjusted scale 455. The sequence depth viewer also includes a second scale 456 on the y-axis indicating the number of sequencing passes represented by the graph.

The manner in which this depth of coverage information is depicted provides a further illustration of the power of a graphical viewer in accordance with the present invention in presenting information in a highly effective manner. A user of the graphical viewer is able to very quickly, at a glance, assimilate useful information relating to the confidence to be attributed to the sequence information depicted in the other panels of the viewer. In this preferred embodiment of the present invention, the sequence depth viewer 452 depicts coverage as a sequence distribution graph 454. A particular advantage of this way of depicting of the depth of coverage information is that it is particularly effective for clearly providing this information in a graphical format which makes a clear visual impression and renders the data easily quantifiable, with reference to the y-axis scale 456. The coverage data for various regions is also easily compared in this format.

In other embodiments of the invention, a sequence depth viewer may graphically depict depth of coverage information in other ways. For example, the actual sequences from which the contig was assembled may be depicted. This way of depicting the sequence coverage information may provide useful information for some users who are concerned with the data acquisition process, for example, used in the contig's formation.

Figure 6:
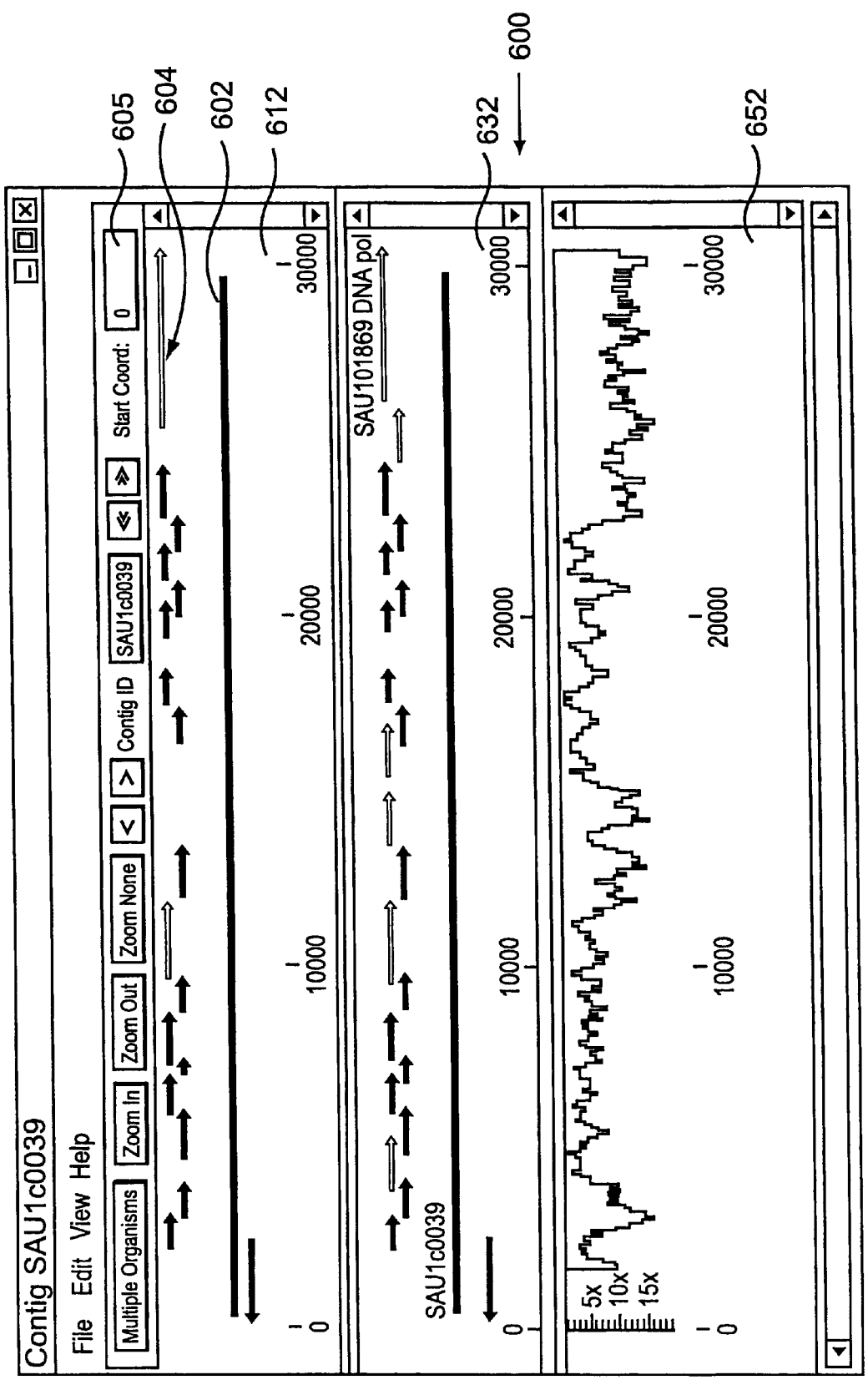
FIG. 6 is a screen shot depicting a main page of a biomolecular sequence graphical viewer modified to illustrate the new starting coordinate feature in accordance with one embodiment of the present invention.
Figure 7:
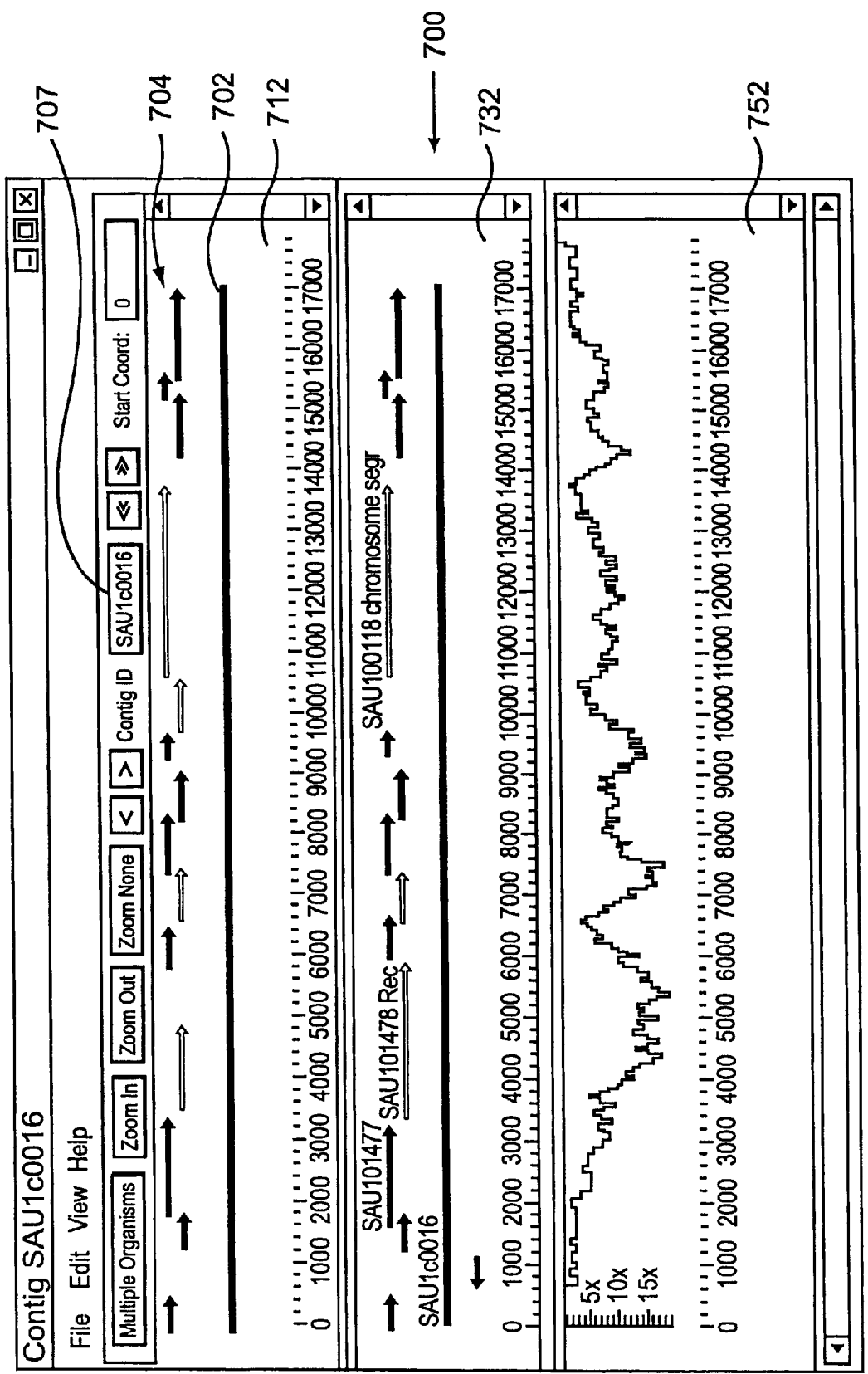
FIG. 7 is a screen shot depicting a main page of a biomolecular sequence graphical viewer modified to illustrate the new ContigID feature in accordance with one embodiment of the present invention.

As noted above, the graphical viewer page 400 includes several buttons and windows along the top 403 of the page 400 for accessing and displaying additional information. Several of these have already been discussed, including the Start Coord 405 and ContigID 407 windows. FIGS. 6 and 7 illustrate additional features of a this embodiment of a graphical viewer in accordance with the present invention.

In addition to displaying the start coordinate for the contig sequence displayed in the legend viewer 612, the Start Coord window 605 may receive an entry from a user of a different starting coordinate. The entry of a different start coordinate will bring a different portion of a contig's sequence into view in the legend viewer. For example, FIG. 6 shows a graphical viewer page 600 with the same settings as page 400, except that 0 has been entered in the Start Coord window 605. As a result, the contig sequence 602 and associated loci 604 shown in the legend viewer 612 is shifted 4467 base pairs upstream to the beginning of contig SAU1c0039. The 4467-most downstream base pairs in the depiction of the contig 414 in FIG. 4 are no longer visible in the viewer of page 600. The corresponding views are also depicted by the target viewer 632 and the sequence depth viewer 652.

Also, in addition to identifying the contig depicted in the viewer 402, the ContigID window 407 may receive an entry from a user of a different ContigID. The entry of a different ContigID will cause the default number of base pairs (preferably starting from the coordinate 0) of the contig sequence associated with the new ContigID to be loaded from the database associated with the viewer and displayed. For example, FIG. 7 shows a graphical viewer page 700 with the ContigID SAU1c0016 entered in the ContigID window 707. As a result, the contig sequence 702 and associated loci 704 shown in the legend viewer 712 are that for contig SAU1c0016. The corresponding views are also depicted by the target viewer 732 and the sequence depth viewer 752.

As also noted above, the graphical viewer 400 includes a menu bar 404 for accessing pull-down menus listing various command and control functions. The File pull-down menu lists standard commands found in applications software packages such as save and print, etc. The Edit pull-down menu provides a list of categories for editing the parameters of the graphical viewers, including the default contig sequence length display number and the colors used to represent various features in the viewers.

Figure 8A:
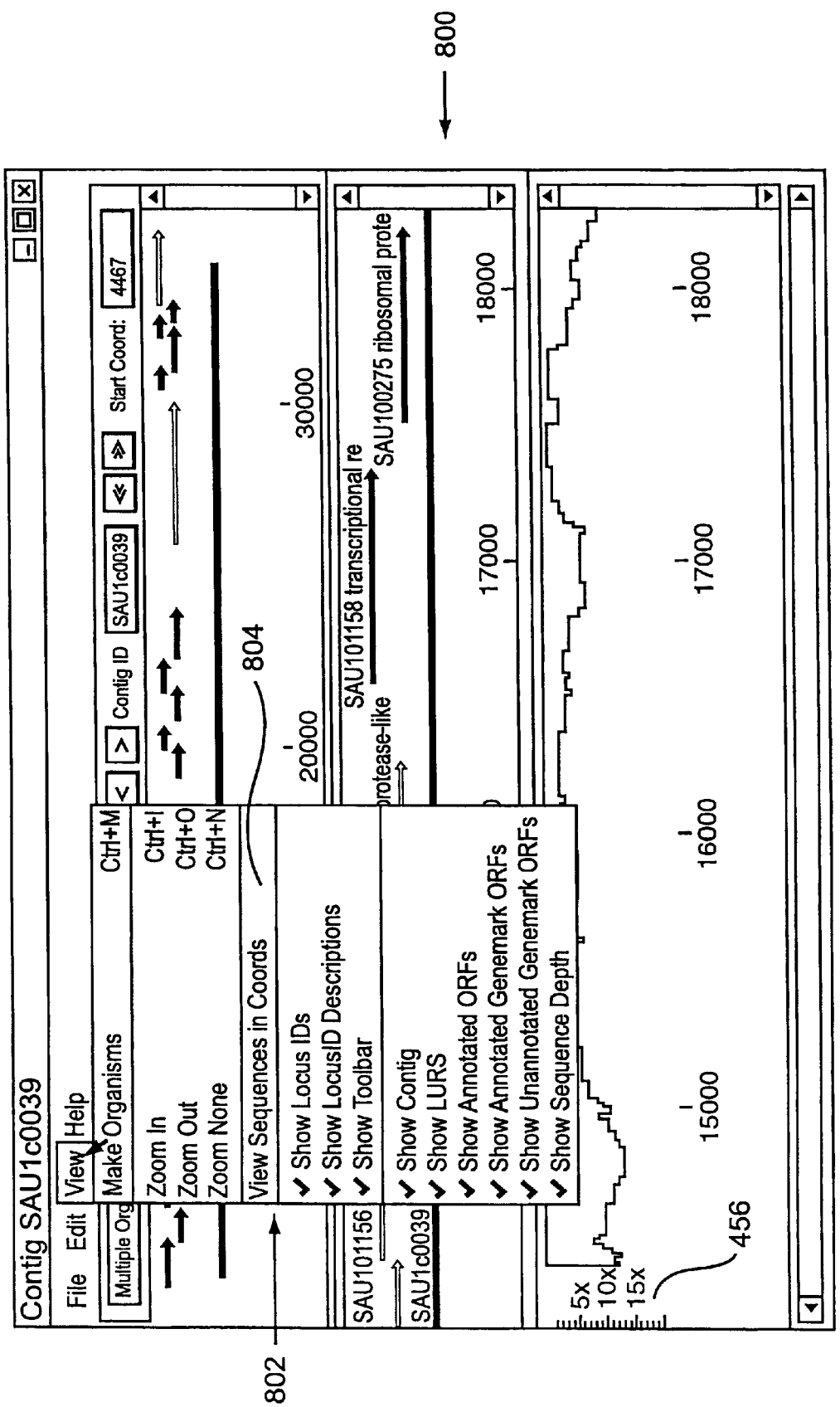
FIGS. 8A–8C are screen shots depicting pages of a biomolecular sequence graphical viewer illustrating a feature which displays an actual biomolecular sequence in accordance with one embodiment of the present invention.
Figure 8B:
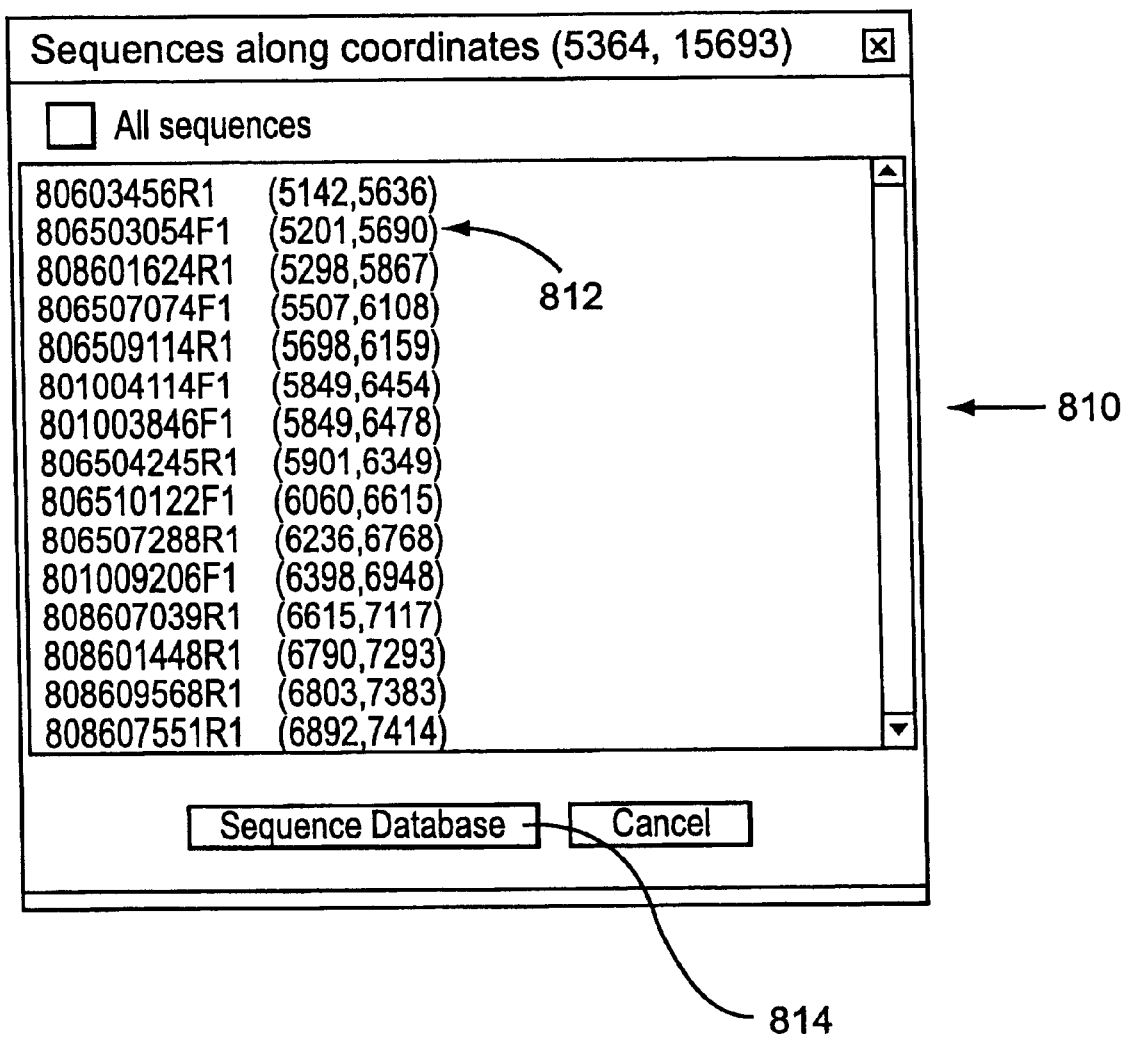
Figure 8C:
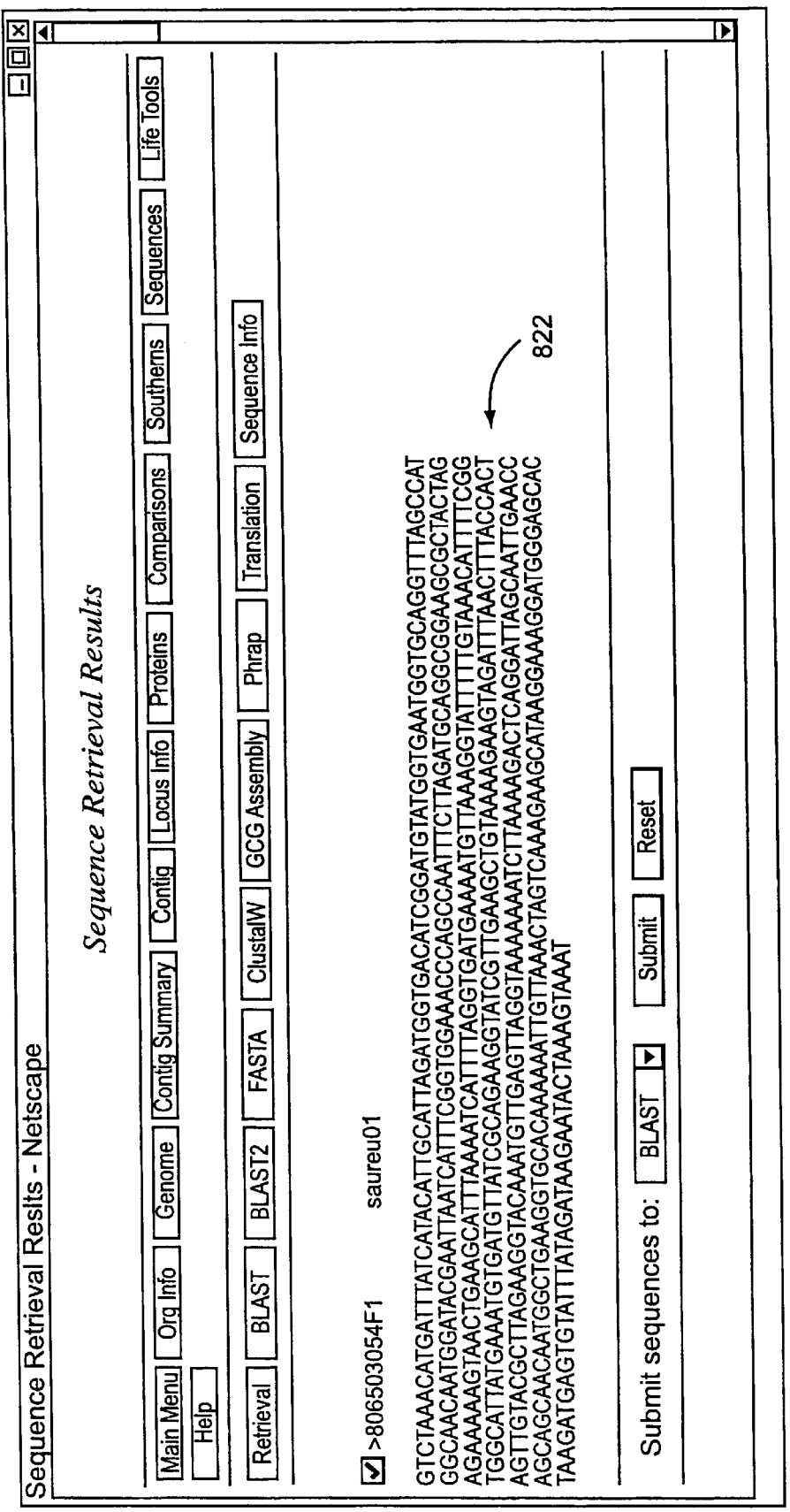

Of particular interest is the View pull-down menu which, together with allowing the user to select which features should be included in the various viewer displays, also includes a View Sequences on Coords 804 option. A graphical viewer page 800 is shown in FIG. 8A with the View pull-down menu 802 selected. Selection of the View Sequences on Coords 804 option from the menu 802 accesses a page 810 listing the sequences used to assemble the contig depicted in the graphical viewer 402, together with the coordinates of each sequence which indicate its coverage. Selecting a sequence from the list, such as the second one in the list, 806503054F1 (5201,5690) 812, and clicking the Sequence Database button 814 accesses a database of the raw sequences used to assemble contigs in the database system associated with the graphical viewer and returns a Sequence Retrieval Results page 820, depicted in FIG. 8C. The Sequence Retrieval Results page 820 depicts the actual nucleotide sequence 822 of the sequence 812 selected in FIG. 8B.

Figure 9:
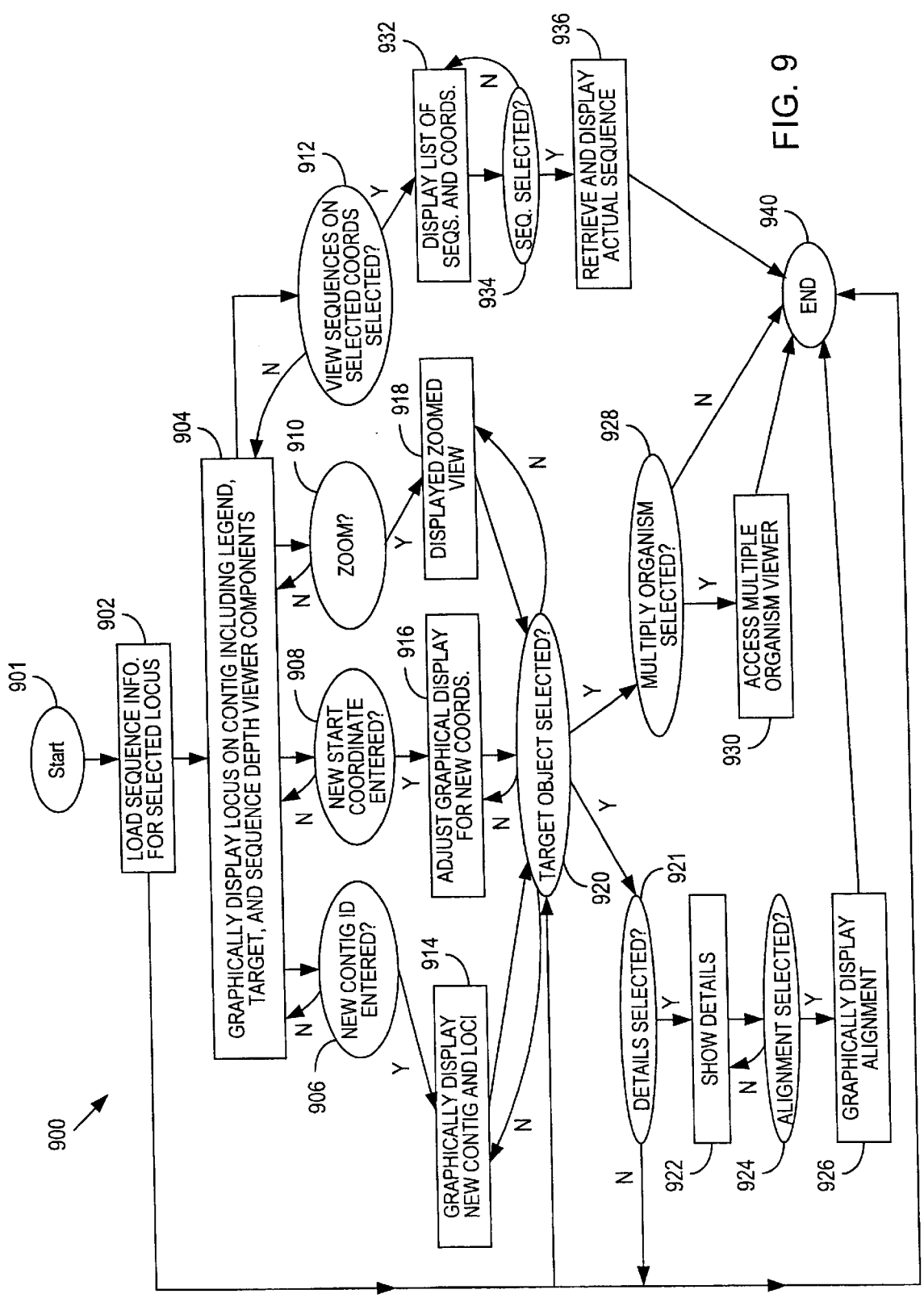
FIG. 9 is a flow chart depicting a process flow by which gene locus information may be viewed with a biomolecular sequence graphical viewer in accordance with a preferred embodiment of the present invention.

A generalized process by which a graphical viewer system in accordance with a preferred embodiment of the present invention returns graphical representations of gene locus information to a user is depicted in FIG. 9. This process flow shows only some of the main features of a preferred embodiment of the present invention in order to illustrate in process flow form some of the options for graphically displaying sequence data in accordance with an embodiment of the present invention. It is not intended to provide a comprehensive depiction of the present invention.

The process 900 begins at 901 and at a step 902 data for a selected locus and its associated contig are loaded into the graphical viewer. As noted above, the locus may be selected from a list in a HTML page provided as part of the user interface of a biomolecular sequence relational database in connection with which the graphical viewer is used, in this case a microbial genomic database. At a step 904, a graphical display of the selected locus on its contig is provided. Preferably, the graphical display has a plurality of components for representing different aspects of the biomolecular sequence data associated with the selected locus. In a particularly preferred embodiment depicted in FIGS. 4A and 4B and described above, the graphical representation is a viewer having three components: a legend viewer, a target viewer, and a sequence depth viewer.

If no further entries or zoom adjustments are made, the process may end at step 940 following the graphical display at step 904. However, a user may want to use the graphical viewer to extract and display additional information relating to the selected locus or other loci, and the viewer provides additional functionalities for this purpose.

The graphical representation of the data displayed by the graphical viewer may be modified in a variety of ways. Also, additional information may be accessed by selecting various objects (namely, loci) in a viewer. For example, a user may enter a new contigID in a field provided in a graphical viewer page, such as window 407 in FIG. 4A. If so, decision step 906 is answered in the affirmative and the new contig and its loci are graphically depicted in a viewer at a step 914. A user may also enter a new start coordinate, such as in Start Coord window 405 in FIG. 4A. If so, decision step 908 is answered in the affirmative and the graphical display is adjusted to show the contig in the new coordinate range at a step 916. In addition, as described above, a user may choose to focus in on a particular portion of a graphically depicted contig. If so, decision step 910 is answered in the affirmative and the graphical display in the target viewer, in this embodiment, is adjusted to show the contig in the zoomed view at a step 918. If any of these decision steps are answered in the negative the graphical viewer display remains unchanged.

After any of these actions, or in the alternative, a user may select an object to obtain further information. In a preferred embodiment, the loci depicted in a target viewer component of the graphical viewer may be selected by clicking on its representation. If so, decision step 920 is answered in the affirmative and the depiction of the locus in the target viewer may be highlighted with a colored box. If a user wishes to obtain detailed information about the selected loci, the user may do so by double clicking on the depiction of that locus. If so, decision step 921 is answered in the affirmative and a Java® page showing detailed information about the selected locus is shown at a step 922.

Another feature of this aspect of a preferred embodiment of the present invention is a graphical alignment viewer, as described above. A user may elect to display a graphical viewer which shows the alignment of the amino acid sequence of the loci of interest against some homologous sequences. If so, decision step 924 is answered in the affirmative and the alignment is graphically displayed in a graphical viewer at a step 926.

A user may also be provided with the option of displaying a multiple organism viewer to view graphical representations of homologous and paralogous loci of the locus of interest. For example, if decision step 920 is answered in the affirmative, a multiple organism viewer may be accessed at a step 930 when a decision step 928 is answered in the affirmative. Further details of the operation of a multiple organism viewer in accordance with a preferred embodiment of the present invention are described below with reference to FIGS. 10A–10E and 11.

Of course the selected object details and multiple organism selection decisions are independent of each other and could just as easily have been presented in other ways in FIG. 9. Further, it should be noted that the system allows the user to exit from the graphical viewer mode at any time. This option is not depicted in FIG. 9.

A further option available for accessing further information from a graphical viewer in accordance with the present invention is the display of actual nucleotide or amino acid sequences for a selected sequence associated with the locus of interest and its contig. In a preferred embodiment, a user may choose this option by clicking on a button in a graphical viewer page such as depicted in FIG. 4A. If so, decision step 912 is answered in the affirmative and a list of sequences sequence identifiers) and coordinates for the sequences from which the contig displayed in the viewer was assembled is displayed at a step 932. A user may then select a sequence from the list. If so, decision step 934 is answered in the affirmative and the actual nucleotide sequence (in this case) of the selected sequence is displayed. The process ends at 940.

As with other data displayed in graphical viewers in accordance with the present invention, the data used in this aspect of the invention is obtained from an associated biomolecular sequence database and system. The organization and operation of such systems may vary. Examples are provided in the Incyte Pharmaceuticals applications previously incorporated by reference herein. Given the description of the functionality and displays herein, one of skill in the art would be able to implement the graphical viewer of the present invention in any such system.

Multiple Organism Viewer

As noted above, a graphical viewer in accordance with the present invention may also provide for the graphical representation and comparison of multiple portions of the genome of one or more organisms based on a locus of interest and its corresponding paralogs (related loci from other portions of an organism's genome) and homologs (related loci from another organism's genome). A preferred embodiment of such a multiple organism viewer is described with reference to FIGS. 10A–10D, below.

Figure 10A:
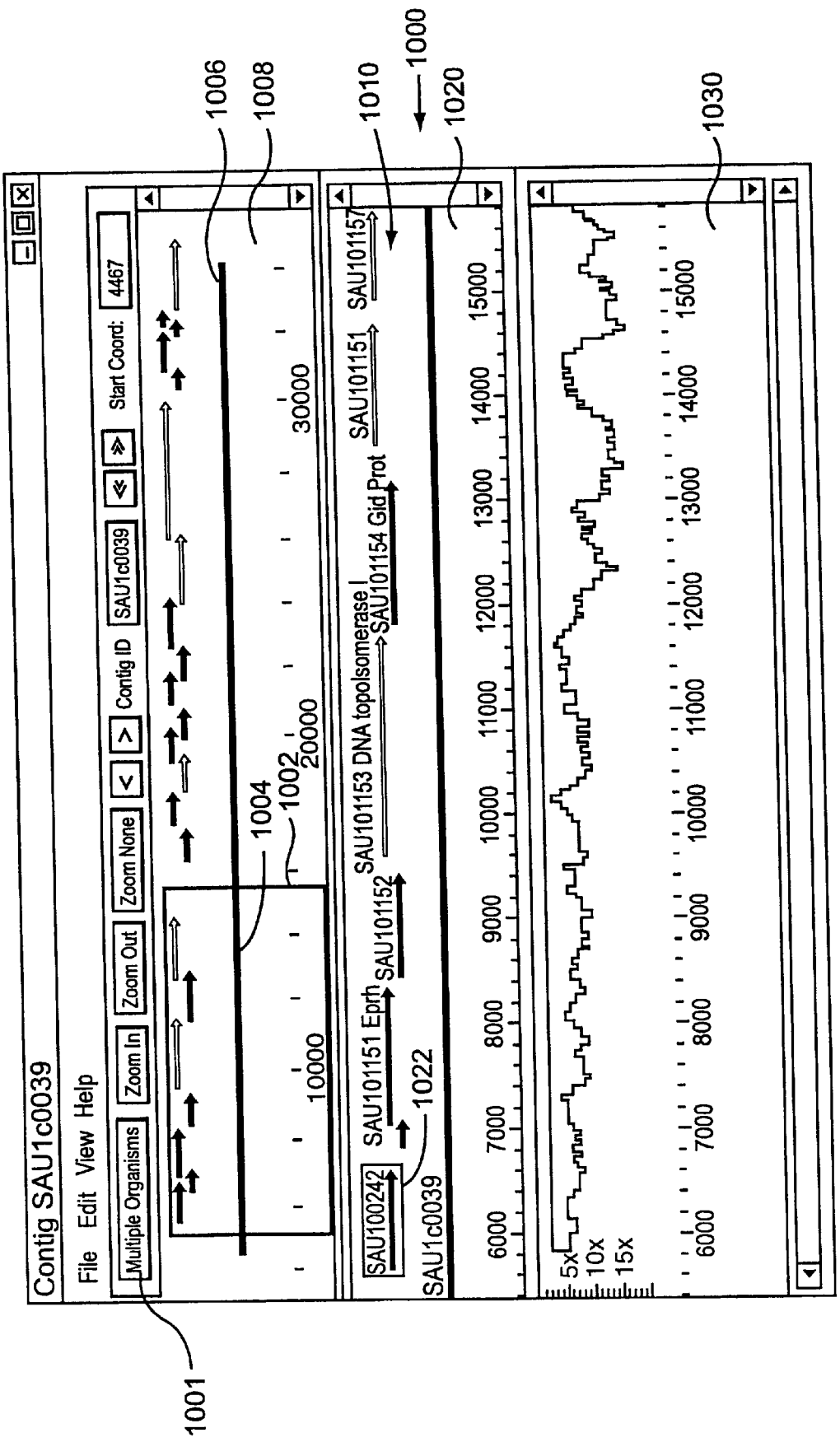
FIGS. 10A–10E are screen shots depicting the operation of a multiple organism biomolecular sequence graphical viewer in accordance with one embodiment of the present invention.

FIG. 10A depicts a main graphical viewer page 1000, like that shown in FIGS. 4A and 4B. In FIG. 10A, a box ("rubber band") 1002 has been placed around a region 1004 of the portion of the contig 1006 displayed by the legend viewer 1008 component of the graphical viewer 1010. This region 1004 of the contig 1006 is displayed by the target viewer 1020 component of the graphical viewer 1010, and its coverage is depicted by the sequence depth viewer 1030 component. In the target viewer 1020, a box 1022 around locus SAU100242 indicates that that locus has been selected. As noted previously, the main viewer page 1000 includes a Multiple Organisms button 1001.

Figure 10B:
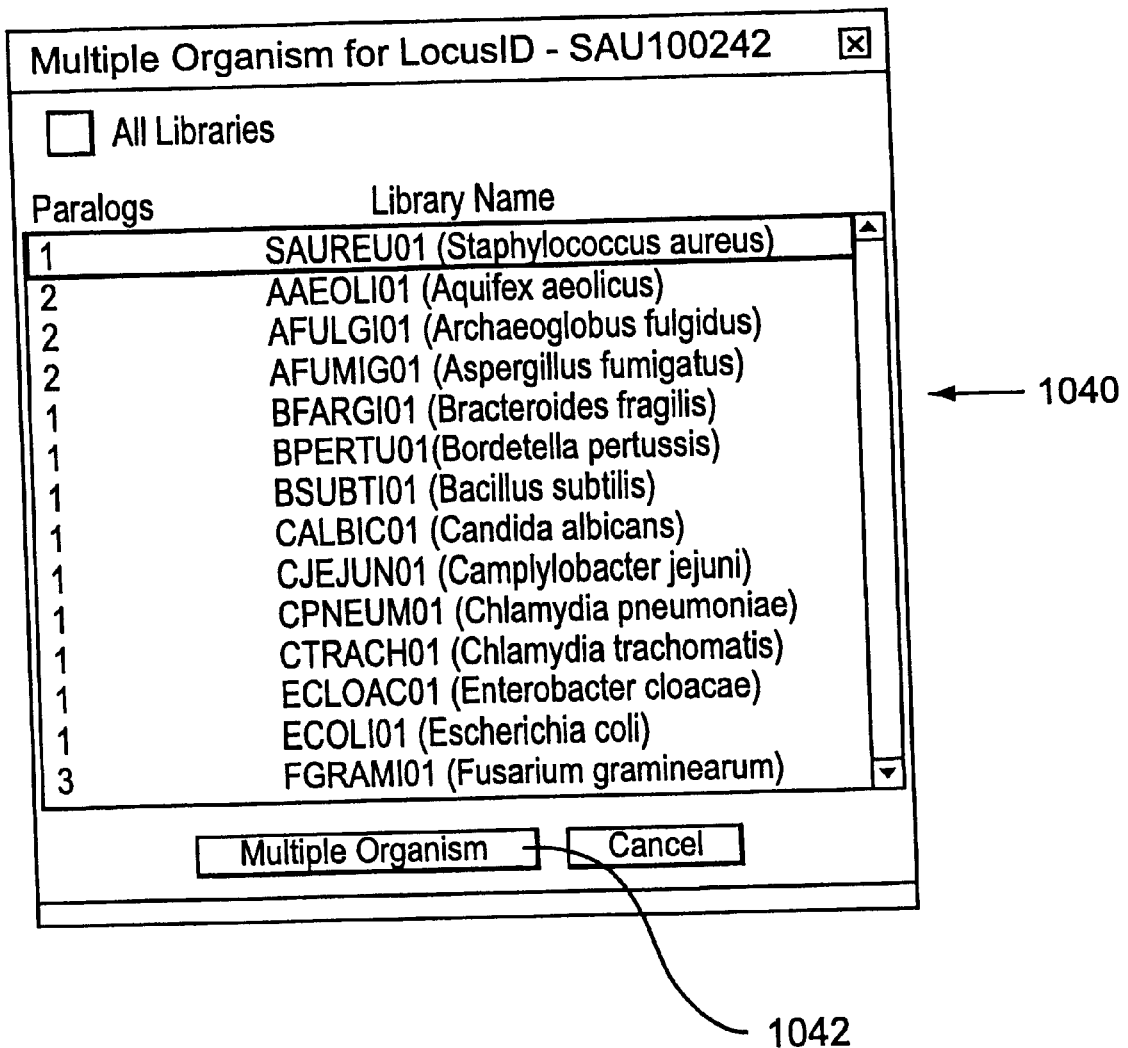
Figure 10C:
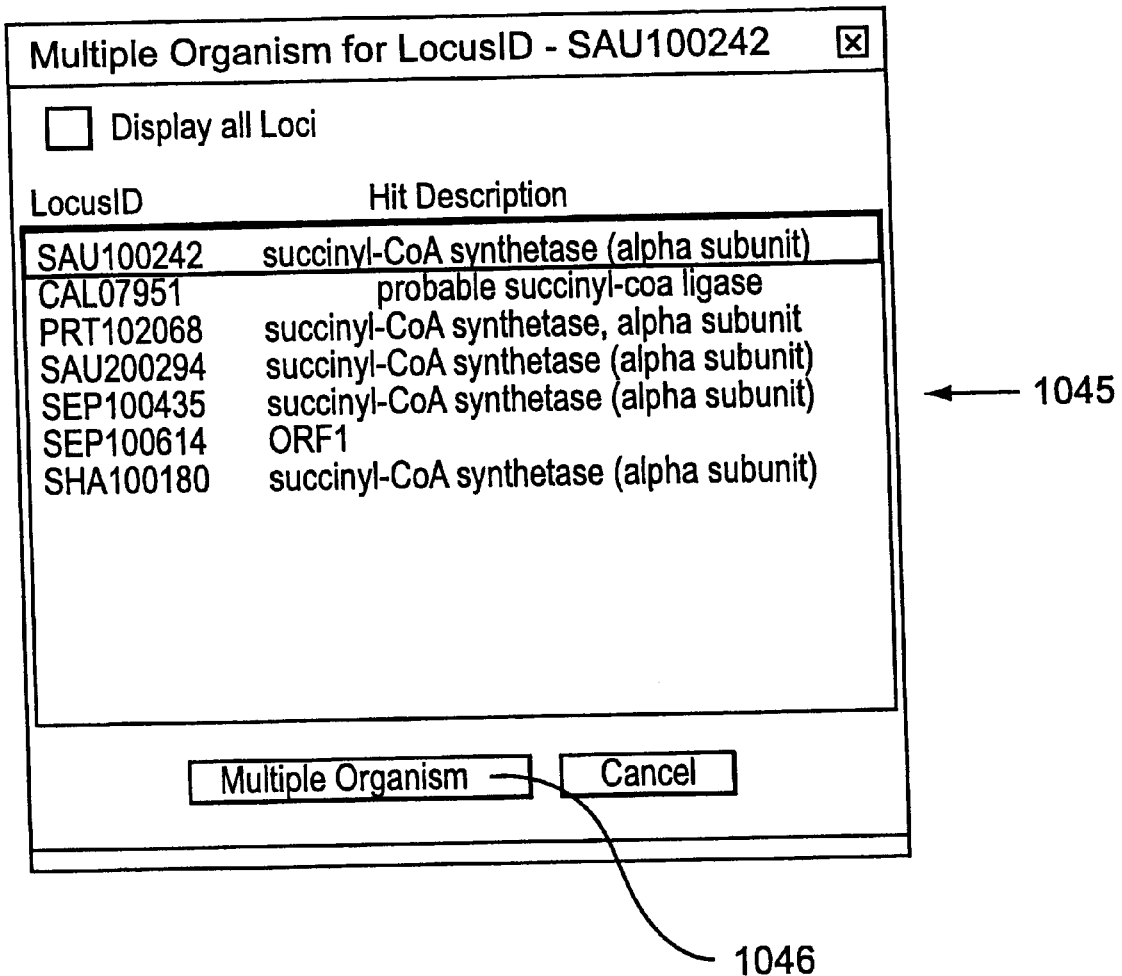

Clicking on the Multiple Organisms button 1001 when a locus has been selected in the target viewer retrieves from the database associated with the viewer and displays a list of all libraries containing homologs and paralogs of the selected locus. FIG. 10B depicts a window 1040 showing a list of libraries retrieved for the locus SAU100242 selected in the previous page shown in FIG. 10A. To access a list of individual homologs and paralogs, a user may select one or more libraries in the list displayed in this window 1040. Clicking on the Multiple Organisms button 1042 retrieves the individual homologs and/or paralogs and displays them. FIG. 10C depicts an example of a window 1045 showing a list of homologs and paralogs for the locus SAU100242 from the libraries selected in screen 1040 shown in FIG. 10B. A hit description for each locus is also provided.

Figure 10D:
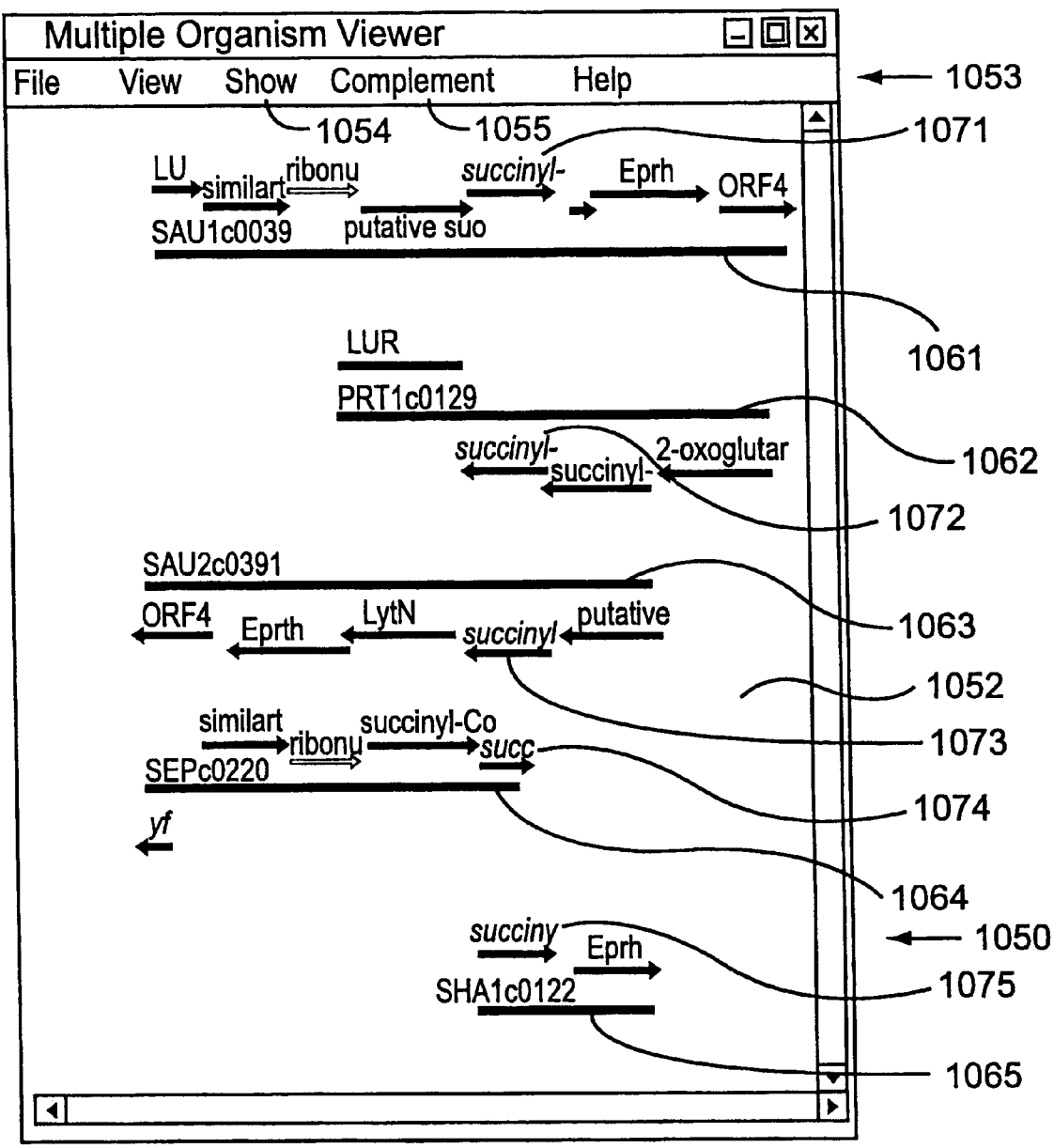

A user may then choose to produce a graphical display of the originally selected locus (e.g. SAU100242) and the selected homologous and paralogous loci displayed in the list of FIG. 10C. By clicking on the Multiple Organisms button 1046 in window 1045, the locus of interest and its homologs and paralogs are loaded into a multiple organism viewer in accordance with a preferred embodiment of the present invention, and the locus of interest and the selected homologs and paralogs are displayed. FIG. 10D depicts an example of such a multiple organism viewer page 1050.

The multiple organism viewer page 1050 provides a single panel multiple organism viewer 1052 graphically depicting the selected locus of interest (SAU100242) on its contig (SAU1c0039) and the selected homologous and paralogous loci on their respective contigs. FIG. 10D, shows a viewer 1052 graphically displaying five (5) contigs in a single page: SAU1c0039 1061 PRT1c0129 1062, SAU2c0391 1063, SEP1c0220 1064, and SHA1c0122 1065. Contig 1061 is shown together with its loci, including the selected locus SAU100242 1071 depicted in bold and italicized in order to more clearly identify it. In the embodiment depicted in FIG. 10D, the loci are annotated with a hit description rather than a Locus ID. Each of the other contigs is also depicted with its loci alongside, and with the loci homologous to SAU100242 (respectively, loci 1072, 1073, 1074 and 1075) shown in bold italics.

The multiple organism viewer 1052 illustrates another example of the power of a graphical viewer in accordance with the present invention to convey biomolecular sequence information in an effective way. As noted above, the selected locus and its homologous and paralogous loci may be shown bold and italicized, or in other type, such as a particular color, in order to distinguish them as the loci of interest. As may also be seen in FIG. 10D, the loci of interest for the graphically displayed contigs are aligned in the page 1052 so that a visual comparison of adjacent loci on the various contigs is easily achieved. This visual representation may be further enhanced through use of the complement feature described below with reference to FIG. 10E.

Further features of such a graphical viewer in accordance with this embodiment of the invention may be accessed by clicking on pull-down menu selections 1053 provided in the multiple organism viewer page 1050. The menu selections include File, View and Help selections that provide features such as described above with reference to FIG. 4A. The Show selection 1054 accesses a list of all of the loci listed in the window illustrated in FIG. 10C and loaded into the multiple organism viewer. By selecting a locus from the Show pull-down menu, a user may determine that the locus along with the contig on which it resides will be displayed or hidden clicking on the loci, a user may determine that a locus will be displayed or hidden. The Show menu may also provide for the same determination to be made with respect to the contigs.

Figure 10E:
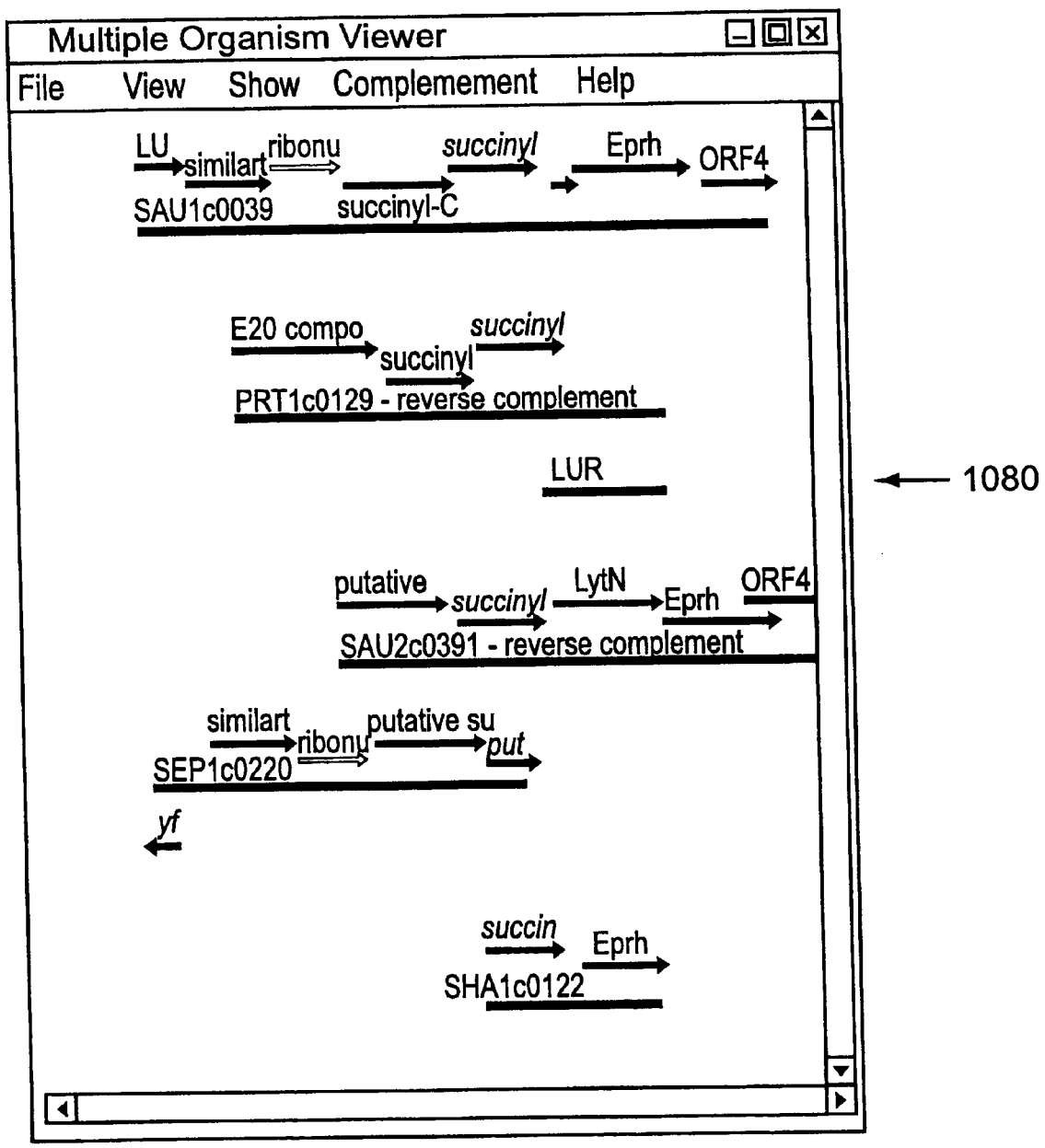

The Complement menu selection 1055 allows a user to manipulate the graphical representations of the contigs and loci in order to facilitate the extraction of salient information from the data. In particular, the complement menu selection 1055 allows the user to perform a reverse complement on any of the contigs displayed in the multiple organism viewer 1052. In this way, the homologous and paralogous loci displayed in the viewer 1052 may be shown in the same reading direction so that a user may more easily locate patterns of related loci adjacent to the loci of interest. FIG. 10E depicts a multiple organism viewer page 1080 in which the loci of interest depicted in page 1050 are shown with the same reading direction by use of the complement feature to show the reverse complement of contigs 1062, 1063 and 1065.

Shortcuts for the complement feature, as well as other features described herein, may be made available to a user according to methods well known to those of skill in the art. For example, the complement of a locus (contig) may be shown by holding down the shift key on a keyboard used to interface with the computer system on which the graphical viewer in operating while clicking on the contig.

Figure 11:
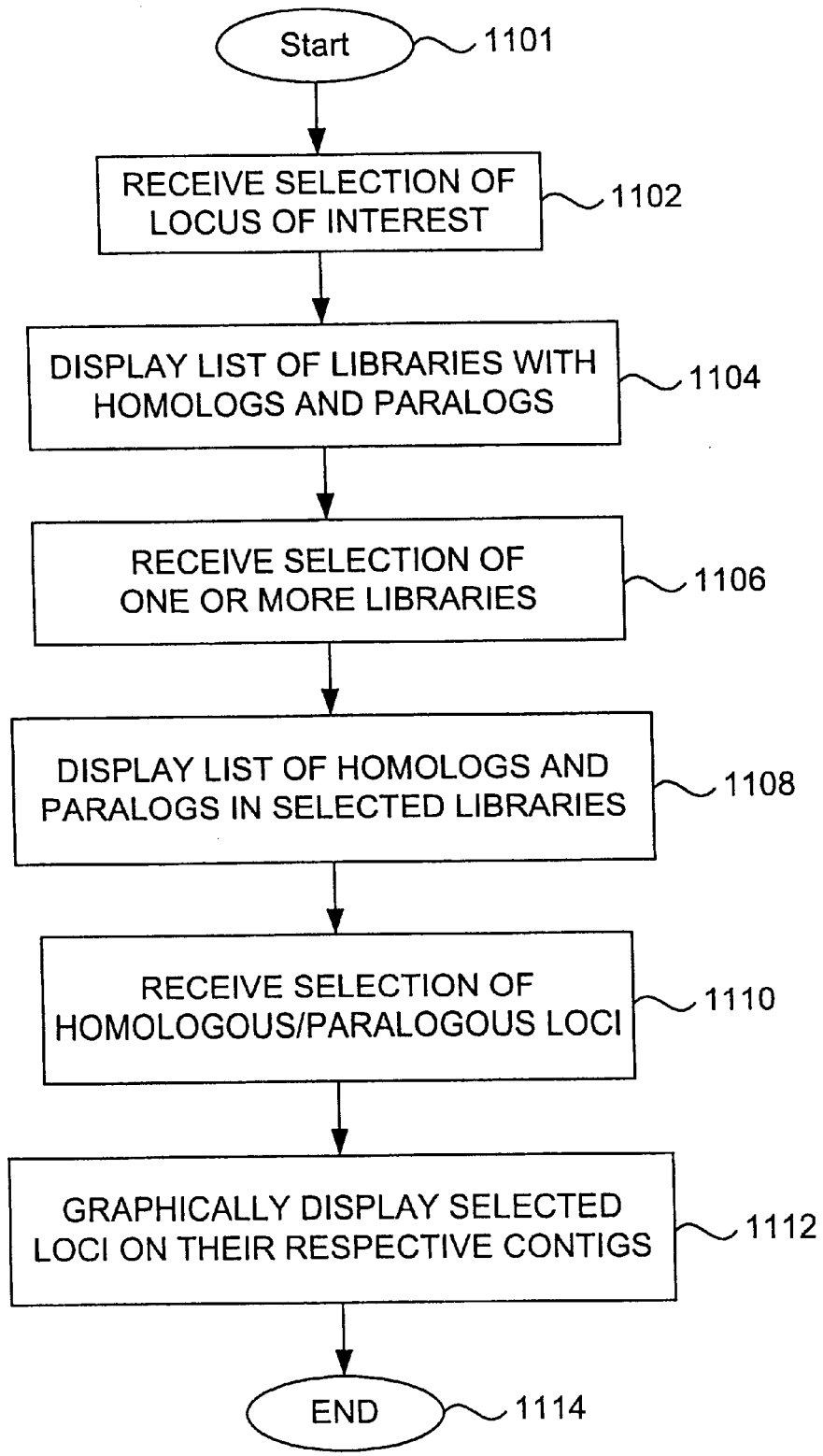
FIG. 11 is a flow chart depicting a process flow by which multiple organism gene locus information may be viewed with a biomolecular sequence graphical viewer in accordance with a preferred embodiment of the present invention.

FIG. 11 depicts a flow chart for a generalized process of the operation a multiple organism viewer in accordance with a preferred embodiment of the present invention. The process 1100 starts at 1101, and at a step 1102 the multiple organism viewer system receives a selection of a locus of interest, for example by clicking on a locus in the target viewer of FIG. 10A. At a step 1104, a list of libraries containing loci homologous or paralogous to the selected locus of interest is displayed in a window. This display may be initiated by a user clicking on a button, such as the Multiple Organisms button in FIG. 10A. Next, the system receives a selection of one or more libraries from the list at a step 1106, and at a step 1108 a list of loci from the selected libraries which are homologous or paralogous to the selected locus of interest is displayed in a window. At a step 1110, the system receives a selection of loci homologous or paralogous to the selected locus of interest from the list to be displayed. Then, at a step 1112, the selected loci and their respective contigs are graphically displayed in a multiple organism graphical viewer. In a preferred embodiment, the viewer shows all of the contigs and loci in a single panel in order to facilitate comparison of the graphically depicted data. The process ends at 1114.

Implementation

It is important to note that the present invention may be implemented as a system or a method, and may be embodied on a variety of computer-readable media that include program instructions, etc. for performing various operations described herein. As noted above, the system implementation is preferably in association with a biomolecular sequence relational database system. The method is a computer-implemented method, generally involving the operation of such a system. The media may be any computer-readable media. Examples of computer-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave travelling over an appropriate medium such as airwaves, optical lines, electric lines, etc.

Conclusion

Although the foregoing invention has been described in some detail for purposes of clarity of understanding, it will be apparent that certain changes and modifications may be practiced within the scope of the appended claims. It should be noted that there are many alternative ways of implementing methods, media and systems of the present invention. As noted previously, the scope of the invention is not limited to use with a microbial genomic database system such as that in connection with which the invention is primarily described above. Given the description provided herein, one of skill in the art would understand how to use the present invention in connection with a variety of computer-based biomolecular sequence database systems. For example, a graphical viewer in accordance with the present invention may be used in connection with database systems employed to store and analyze other types and forms of nucleic acid sequences or expressed nucleic acid or amino acid sequences. Accordingly, the present embodiments are to be considered as illustrative and not restrictive, and the invention is not to be limited to the details given herein, but may be modified within the scope and equivalents of the appended claims.

What is claimed is:

1. A method implemented in a computer system for presenting biomolecular sequence data, comprising:
retrieving biomolecular sequence data, the data including nucleic acid sequences from an organism's genome representing one or more open reading frames, from a database in response to a user query; and
graphically depicting elements of the biomolecular sequence data in a user interface for said computer system.

2. A method implemented in a computer system for presenting biomolecular sequence data, comprising:
retrieving biomolecular sequence data from a database in response to a user query; and
graphically depicting elements of the biomolecular sequence data in a user interface for said computer system, wherein said graphical depiction comprises a plurality of panels, at least one of said plurality of panels graphically depicting depth of coverage information for a portion of a biomolecular sequence depicted in at least one other of said plurality of panels.

3. The method of claim 2, wherein said plurality of panels are comprised within a single frame.

4. The method of claim 3, wherein said plurality of panels provide graphical depictions representing different aspects of said biomolecular sequence data.

5. The method of claim 4, wherein said biomolecular sequence data comprises gene locus data.

6. The method of claim 5, wherein said plurality of panels comprises three panels.

7. The method of claim 6, wherein said three panels comprise a first panel graphically depicting at least a portion of a contig and its associated loci, a second panel graphically depicting at least a portion of the contig depicted in said first panel and annotated loci associated with the portion, and a third panel graphically depicting depth of coverage information for the portion of the contig depicted in the second panel.

8. The method of claim 2, wherein said method is implemented in Java programming language.

9. A method implemented in a computer system for presenting biomolecular sequence data, comprising:
retrieving biomolecular sequence data for a plurality of homologous loci, the data including nucleic acid sequences from an organism's genome representing one or more open reading frames, from a database in response to a user query; and
graphically depicting at least some of the homologous loci in a user interface for said computer system.

10. The method of claim 9, wherein said graphical depiction comprises a single panel.

11. A computer system, comprising:
a database containing biomolecular sequence data;
a user interface configured to
receive a query relating to the biomolecular sequence data, the data including nucleic acid sequences from an organism's genome representing one or more open reading frames, and
graphically depicting elements of the biomolecular sequence data returned by the query in the user interface for the computer system.

12. A computer system, comprising:
a database including biomolecular sequence data; and
a user interface configured to
receive a query relating to the biomolecular sequence data, and
graphically display the results of said query, wherein said graphical depiction comprises a plurality of panels, at least one of said plurality of panels graphically depicting depth of coverage information for a portion of a biomolecular sequence depicted in at least one other of said plurality of panels.

13. The system of claim 12, wherein said plurality of panels are comprised within a single frame.

14. The system of claim 13, wherein said plurality of panels provide graphical depictions representing different aspects of said biomolecular sequence data.

15. The system of claim 14, wherein said biomolecular sequence data comprises gene locus data.

16. The system of claim 15, wherein said gene locus data is depicted in three panels comprising a first panel graphically depicting at least a portion of a contig and its associated loci, a second panel graphically depicting at least a portion of the contig depicted in said first panel and annotated loci associated with the portion, and a third panel graphically depicting depth of coverage information for the portion of the contig depicted in the second panel.

17. A computer-readable medium containing programmed instructions arranged to graphically display biomolecular sequence data, the computer-readable medium including programmed instructions for:
retrieving biomolecular sequence data from a computer system database in response to a user query; and
graphically depicting elements of the biomolecular sequence data in a user interface for the computer system, wherein said graphical depiction comprises a plurality of panels, at least one of said plurality of panels graphically depicting depth of coverage information for a portion of a biomolecular sequence depicted in at least one other of said plurality of panels.

* * * * *